(12) United States Patent  (10) Patent No.: US 7,529,339 B2
Goldman et al.  (45) Date of Patent: May 5, 2009

(54) METHOD AND SYSTEM FOR OPTIMIZING DOSE DELIVERY OF RADIATION

(75) Inventors: Samuel Pedro Goldman, London (CA); Jeff Z. Chen, London (CA); Jerry J. Battista, London (CA)

(73) Assignee: University of Western Ontario, London, Ontario (CA)

( * ) Notice: Subject to any disclaimer, the term of this patent is extended or adjusted under 35 U.S.C. 154(b) by 77 days.

(21) Appl. No.: 11/743,273

(22) Filed: May 2, 2007

(65) Prior Publication Data

US 2007/0201614 A1 Aug. 30, 2007

Related U.S. Application Data

(63) Continuation-in-part of application No. 10/581,885, filed as application No. PCT/CA2004/002108 on Dec. 10, 2004.

(60) Provisional application No. 60/528,775, filed on Dec. 12, 2003, provisional application No. 60/566,433, filed on Apr. 30, 2004, provisional application No. 60/602,631, filed on Aug. 19, 2004.

(51) Int. Cl.
*A61N 5/10* (2006.01)
(52) U.S. Cl. ...................................... 378/65
(58) Field of Classification Search .............. 378/65
See application file for complete search history.

(56) References Cited

U.S. PATENT DOCUMENTS 6,038,283 A 3/2000 Carol et al.
6,152,599 A * 11/2000 Salter, Jr. .................. 378/209
6,546,073 B1 4/2003 Lee (Continued)

FOREIGN PATENT DOCUMENTS

CA 2587587 6/2005

(Continued)

OTHER PUBLICATIONS

Spirou et al., "Smoothing intensity-modulated beam profiles to improve the efficiency of delivery", Medical Physics, vol. 28, Issue 10, Oct. 2001, pp. 2105-2112.*

(Continued)

*Primary Examiner*—Chih-Cheng G Kao
(74) *Attorney, Agent, or Firm*—Bereskin & Parr LLP; Ian C. McMillan

(57) ABSTRACT

Described embodiments relate to determining an objective function to be used for mapping radiation beams to a patient body volume. The objective function has a first term related to at least one target volume and a second term related to at least one non-target volume. The second term is zero only when a product of the weight of a beamlet mapped to pass through a non-target volume portion and the dose deposited by said beamlet is equal to a first predetermined average dose constraint value for the respective non-target volume portion, for all beamlets mapped to pass through the at least one non-target volume. This limit aims to reduce the occurrence of negative beam weights. In another embodiment, the objective function has a smoothing term for biasing the weight of beamlets towards a uniform distribution within the respective beam. Radiotherapy is delivered based on the objective function.

39 Claims, 12 Drawing Sheets

U.S. PATENT DOCUMENTS

| | | | |
|---|---|---|---|
| 6,714,620 | B2 | 3/2004 | Caflisch et al. |
| 2002/0008915 | A1 | 1/2002 | Koster |
| 2002/0080915 | A1 | 6/2002 | Frolich |
| 2003/0212325 | A1 | 11/2003 | Cotrutz et al. |
| 2005/0111621 | A1 | 5/2005 | Riker et al. |
| 2007/0127623 | A1 | 6/2007 | Goldman et al. |

FOREIGN PATENT DOCUMENTS

| | | |
|---|---|---|
| WO | WO 03/099380 | 12/2003 |
| WO | WO 03099380 | 12/2003 |
| WO | WO 2005/057463 | 6/2005 |

OTHER PUBLICATIONS

International Search Report, dated Aug. 5, 2008 from related International Application No. PCT/CA2008/000834.

Examination Report, dated Jul. 4, 2008 from related European Patent Application No. 04802285.9.

Starkschall G: "A constrained least-squares optimization method for . . ." Medical Physics Sep.-Oct. 1984, v. 11, No. 5, Sep. 1984, pp. 659-665, ISBN: 0094-2405.

Censor Y: "Mathematical aspects of radiation therapy treatment planning . . ." Computational Radiology and Imaging: Therapy and Diagnostics, v. 110, 1999, pp. 1-12.

Hilbig Matthias et al.: "Design of an inverse planning system . . ." Zeitschrift fuer medizinische physik, urban und fischer, Jena, v. 12, No. 2, 2002, pp. 89-96, ISBN: 0939-3889.

U.S. Appl. No. 60/528,775, filed Jun. 23, 2005, Goldman et al.

U.S. Appl. No. 60/566,433, filed Jun. 23, 2005, Goldman et al.

U.S. Appl. No. 60/602,631, filed Jun. 23, 2005, Goldman et al.

S Webb, "The physical basis of IMRT and inverse planning," The British Journal of Radiology, 76, 678-689, 2003.

S.P. Goldman, J.Z. Chen, and J.J. Battista, "Fast Inverse Dose Optimization (FIDO) for IMRT via Matrix Inversion with no Negative Intensities," XIVth International Conference on the Use of Computers in Radiation Therapy, pp. 112-115, May 11, 2004.

S.P. Goldman, J.Z. Chen and J.J. Battista, "Feasibility of fast inverse dose optimization algorithm for IMRT via matrix inversion without negative beamlet intensities," Med. Phys. 32(9), 3007-3016, Aug. 30, 2005.

\* cited by examiner

METHOD AND SYSTEM FOR OPTIMIZING DOSE DELIVERY OF RADIATION

CROSS-REFERENCE TO RELATED APPLICATIONS

This application is a continuation-in-part of U.S. Utility patent application Ser. No. 10/581,885 filed Jun. 12, 2006, which is a national phase application of International Application No. PCT/CA2004/002108 filed Dec. 10, 2004, which claims the benefit of U.S. Provisional Patent Application No. 60/602,631 filed Aug. 19, 2004, and the benefit of U.S. Provisional Patent Application No. 60/566,433 filed Apr. 30, 2004, and the benefit of U.S. Provisional Patent Application No. 60/528,775 filed Dec. 12, 2003, the entire contents of all of which are hereby incorporated by reference.

TECHNICAL FIELD

The described embodiments relate to methods and systems for optimizing dose delivery of radiation. In particular, the described embodiments relate to efficient and effective methods of determining a minimum of an objective function for planning dose delivery of radiation.

BACKGROUND

For cancer patients, radiation therapy is recognized as a valuable form of treatment. Radiation therapy involves the transmission of radiation energy to a tumor site within the patient.

Radiation therapy planning may be carried out according to a forward planning technique or an inverse planning technique. Forward planning involves delivering an initial planned radiation dose and then delivering subsequent doses by observation or inference of the efficacy of the preceding dose in a trial-and-error manner. The optimization of dose delivery by forward planning is therefore performed according to human observation and experience. Inverse planning instead seeks to calculate an optimized dose delivery and then work backwards to determine the appropriate radiation beam characteristics to deliver that optimized dose.

Inverse planning of radiation therapy for tumors may be performed for Tomotherapy or Intensity Modulated Radiation Therapy (IMRT) radiation delivery techniques. Both of these techniques involve transmission of radiation beams, usually collimated by a multi-leaf collimator (MLC), toward the tumor site from various angular orientations. For Tomotherapy, a helical arc is employed to irradiate the tumor slice by slice, while for IMRT multiple intensity-modulated conical beams are used to irradiate the tumor from a number of different directions.

In order to ensure that the patient is optimally treated, it is necessary to ensure that the radiation dose is deposited primarily within the tumor volume, rather than in the surrounding tissue or organs. It has been found to be problematic to quickly and reliably determine an optimization so as to maximize the dose delivery to the tumor site while minimizing radiation dose delivery to other organs or tissues.

A fast optimization algorithm is important, not only for designing good radiation treatment plans, but also for the successful implementation of future interactive adaptive treatment techniques. Conventional optimization algorithms using numerical searches, such as the known conjugate gradient search with positive beam weight constraints, usually require many iterations involving long computation times and may result in sub-optimal plans due to trapping in local minima of the objective function.

It is possible to determine a direct solution of the inverse problem using conventional quadratic objective functions, without imposing positive beam weight constraints. This solution is computationally faster but results in unrealistic (negative) beam intensities. Once an ad-hoc condition requiring the beam intensities to be positive is introduced (i.e., by forcing negative intensity values to be zero), the solution of the quadratic objective function by linear algebraic equations yields a radiation therapy dose distribution with significant artifacts. These artifacts may significantly deteriorate an otherwise optimized dose delivery. Accordingly, rather than treat a patient with a sub-optimal dose delivery, the rather more computationally intensive numerical searching has been preferred for finding the minimum of the objective function.

A further drawback of current IMRT plan optimization, is that only about seven to eleven different gantry angles may be employed because present techniques find it too computationally intensive to optimize the objective function for a greater number of beams.

In view of the above shortcomings of existing systems, it is desired to provide a method and system for optimized dose delivery, which addresses or ameliorates one or more of the mentioned shortcomings.

SUMMARY

In one aspect, described embodiments relate to a method of dose delivery of radiation. The method comprises the step of determining an objective function to be used for mapping radiation beams to a body volume comprising at least one target volume, and at least one non-target volume. The objective function comprises a first term related to the at least one target volume and a second term related to the at least one non-target volume. The method further comprises determining a minimum of the objective function.

In some described embodiments, the beams, comprising a plurality of beamlets, mapped to pass through the at least one non-target volume, comprising a plurality of non-target volume portions, are limited such that the second term is zero only if a product of the intensity of a beamlet mapped to pass through a non-target volume portion and the dose deposited by said beamlet is equal to a first predetermined average dose constraint value for the respective non-target volume portion, for all beamlets mapped to pass through the at least one non-target volume.

In other described embodiments, the beams mapped so as to pass through the at least one non-target volume are limited such that the second term is zero only if the weights of beamlets passing through the at least one non-target volume are zero.

Optionally, the objective function employed in the method may further comprise a third term related to at least one organ-at-risk (OAR) volume, whereby beams, comprising a plurality of beamlets, mapped to pass through the at least one OAR volume, comprising a plurality of OAR volume portions, are limited such that the third term is zero only if, a product of the intensity of a beamlet mapped to pass through an OAR volume portion and the dose deposited by said beamlet is equal to a second predetermined average dose constraint value for the respective OAR volume portion, for all beamlets mapped to pass through the OAR volume. The second predetermined average dose constraint value for the respective OAR volume portion may be determined according to constraints derived from a dose-volume constraint curve.

As an additional option, the objective function may further comprise a fourth term for biasing the intensity of the beamlets of a beam mapped to pass through the at least one target volume and the at least one non-target volume towards a uniform distribution within the respective beam. For example, the fourth term may be a local or average smoothing term.

Further described embodiments relate to a method of providing optimized radiation dose delivery. The method comprises the step of determining an objective function to be used for mapping radiation beams, comprising a plurality of beamlets, to at least one target volume. In some described embodiments, the objective function comprises a smoothing term for biasing the intensity of beamlets, for a respective beam mapped to pass through the at least one target volume, towards a uniform distribution within the respective beam. In other described embodiments, the objective function has a symmetry term for enabling symmetrical dose delivery about an axis of the target volume, and providing radiation based on the objective function.

Radiation may then be delivered based on the determined minimum of the objective function.

Other described embodiments relate to a system for optimizing dose delivery of radiation. In some described embodiments, the system comprises an optimization module for determining an objective function to be used for mapping radiation beams to a body volume comprising at least one target volume, and at least one non-target volume. The objective function comprises a first term related to the at least one target volume and a second term related to the at least one non-target volume, the optimization module being arranged to determine a minimum of the objective function whereby beams, comprising a plurality of beamlets, mapped to pass through the at least one non-target volume, comprising a plurality of non-target volume portions, are limited such that the second term is zero only if a product of the intensity of a beamlet mapped to pass through a non-target volume portion and the dose deposited by said beamlet is equal to a predetermined average dose constraint value for the respective non-target volume portion, for all beamlets mapped to pass through the at least one non-target volume. The system further comprises an output operably associated with the optimization module for providing data to a radiation delivery apparatus for delivering radiation to the body volume based on the determined minimum of the objective function.

In other described embodiments, the system comprises computer processing means for determining an objective function to be used for mapping radiation beams to a body volume comprising at least one target volume, and at least one non-target volume. The objective function comprises a first term related to the at least one target volume and a second term related to the at least one non-target volume. The computer processing means is arranged to determine a minimum of the objective function whereby beams mapped so as to pass through the at least one non-target volume are limited such that the second term is zero only if the weights of beamlets passing through the at least one non-target volume are zero. The system further comprises data communication means operably associated with the computer processing means for providing data to a radiation delivery apparatus for delivering radiation to the body volume based on the determined minimum of the objective function.

Still further described embodiments relate to computer readable storage having stored thereon computer program instructions executable on a computer system for causing the computer system to perform a dose optimization method. The dose optimization method comprises determining an objective function to be used for mapping radiation beams for a body volume comprising at least one target volume and at least one non-target volume. The objective function comprises a first term related to the at least one target volume and a second term related to the at least one non-target volume.

In some described embodiments, the method comprises the step of determining a minimum of the objective function whereby beams, comprising a plurality of beamlets, mapped to pass through the at least one non-target volume, comprising a plurality of non-target volume portions, are limited such that the second term is zero only if a product of the intensity of a beamlet mapped to pass through a non-target volume portion and the dose deposited by said beamlet is equal to a first predetermined average dose constraint value for the respective non-target volume portion, for all beamlets mapped to pass through the at least one non-target volume.

In other described embodiments, the method comprises the step of determining a minimum of the objective function whereby beams mapped so as to pass through at least one non-target volume are limited such that the second term is zero only if intensities of beamlets passing through the at least one non-target volume are zero.

Even further described embodiments relate to a method of determining an objective function to be used for mapping radiation beams for a body volume comprising at least one target volume and at least one non-target volume. The objective function comprises a first term related to the at least one target volume and a second term related to the at least one non-target volume. The method comprises determining a minimum of the objective function whereby beams mapped so as to pass through the at least one non-target volume are limited such that the second term is zero only if intensities of beamlets passing through the at least one non-target volume are zero.

In the described embodiments, the radiation delivery may be by IMRT or Tomotherapy.

Described embodiments enable the objective function to be minimized according to the solution of a set of linear algebraic equations. While there are a number of ways to solve a system of linear equations, some embodiments are based on determining the inverse of a beamlet intersection matrix. Because of the method of determining the minimum of the objective function described herein, determining the inverse of the beamlet intersection matrix greatly reduces the possibility of generating anomalous negative beam weights for the beamlets. Moreover, the terms of the objective function itself may greatly reduce the appearance of negative beam weights for the beamlets. Accordingly, the problems associated with negative beam weights and the constraints imposed on optimization methods to avoid them may be obviated to at least some extent.

Described embodiments may also enable the terms of the objective function to be scaled by a respective importance parameter. The importance parameter may be determined according to a function of position within the target or non-target volume, or may alternatively be determined according to a user-configurable value.

Because the technique employed by the described embodiments allow the optimization to be framed as a solution of algebraic linear equations, the lengthy processing time required to search for the global minimum of the objective function is substituted with a significantly improved processing time. This increase in processing efficiency is measurable in orders of magnitude. For example, the present technique can accomplish in seconds or minutes what would take several hours with some prior art techniques. Accordingly, with methods and systems according to the described embodiments, medical staff can greatly reduce the time required for radiation therapy planning while providing a highly optimal dose delivery plan.

The described embodiments enable a larger number of radiation delivery angles to be employed, compared with previous IMRT techniques. This is due to the high computational efficiency with which the optimization can be carried out according to the described embodiments, providing higher quality conformal dose distributions to the tumor site and better quality optimizations in avoiding radiation delivery to organs at risk and other organs or tissues not forming part of the target site.

DETAILED DESCRIPTION

Figure 1:
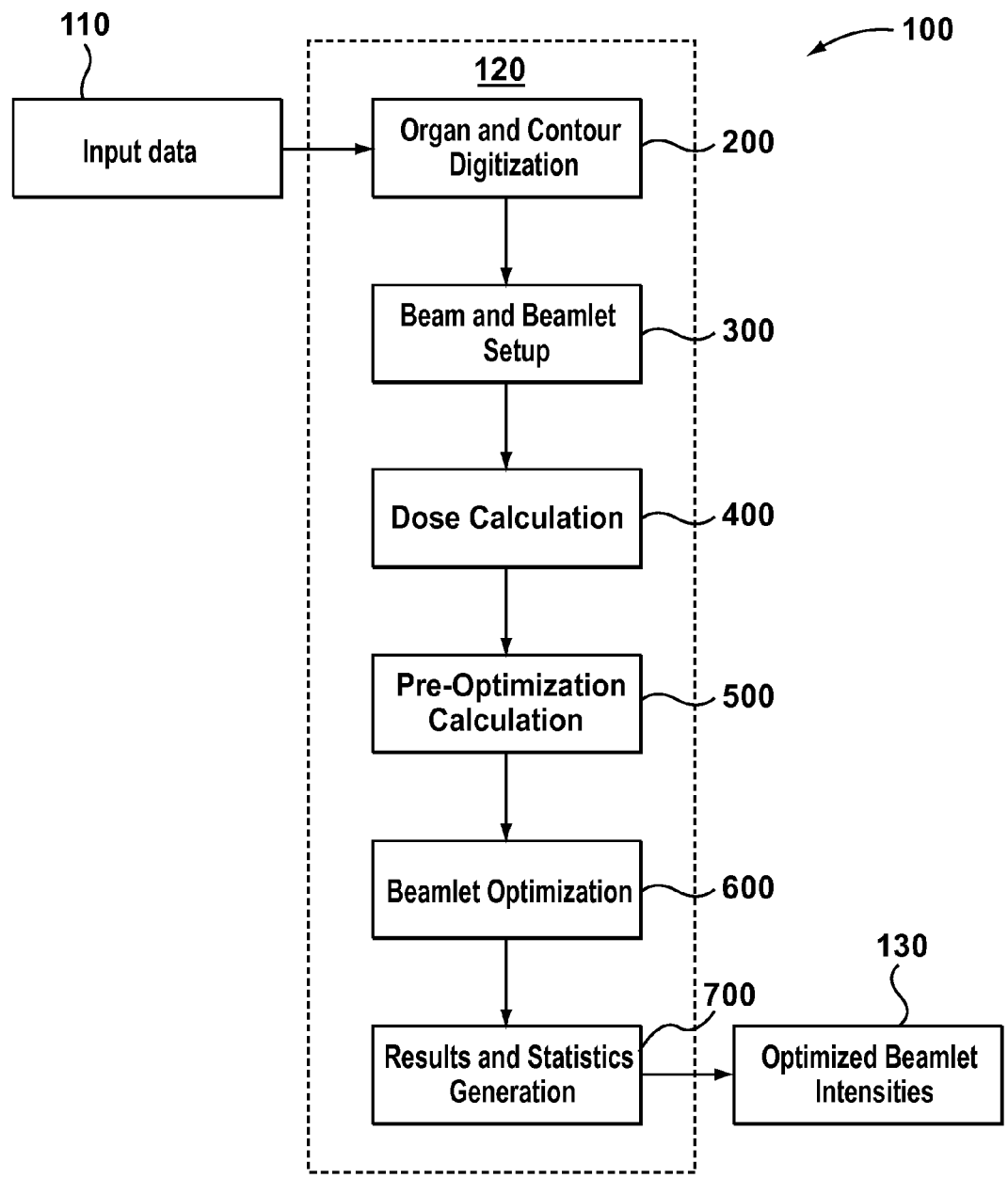
FIG. 1 is a flowchart of an overall process used in dose delivery optimization according to described embodiments.

The described embodiments relate to methods and systems for optimizing dose delivery of radiation therapy to tumor sites within a patient. Typically, the radiation will be directed toward a single tumor site, although it is not uncommon for multiple tumor sites to be treated simultaneously. While embodiments of the present invention are capable of taking into account multiple tumor sites, which are encompassed by the planning target volume (PTV), for simplicity of description, embodiments will primarily be described as they apply to a single PTV. Similarly, only a single organ at risk (OAR) and a single volume of other intervening tissues or organs, which is called herein all-the-rest (ATR), are described.

The number of PTV, OAR and ATR volumes, as well as the size and relative orientation thereof, will vary from patient to patient and according to the desired treatment plan determined by the radiation oncologist. For example, it is possible that the optimization may not have to take account of an organ at risk, or the PTV may be entirely within the organ at risk, with very little ATR volume to take account of.

It will usually be necessary or at least advisable for the supervising radiation oncologist or other suitably qualified medical personnel to determine one or more importance parameters in the objective function by which relative importance may be attributed to certain tissue or organ volumes within the patient relative to the other volumes.

During radiation dose delivery, radiation scattering commonly occurs due to the passage of the radiation through the body volume. These scatter effects are introduced during the computation of the distribution of dose deposited by the radiation. The described computation, preliminary to the optimization, accounts for tissue density inhomogeneity as well. However, embodiments of the optimization method and system described herein apply to any calculation of dose distribution regardless of whether radiation scatter is factored into the calculation or not.

The most fundamental requirements of a radiation treatment optimization are: (i) the dose is homogeneously deposited in the PTV; (ii) the dose deposited in any OAR does not exceed a threshold value and ideally should be zero; (iii) the dose deposited in ATR organs and tissue not included in the PTV and OARs, should be as small as possible and ideally zero to minimize the risk of secondary carcinogenesis; (iv) the dose gradient crossing the PTV boundaries should be as high as possible.

Optimizations are pursued by the minimization of a positive-definite objective function, also sometimes termed an "objectivity function" or a "cost function". A successful optimization will yield a global minimum to this objective function in a short computation time with physically achievable beamlet intensities (i.e. greater than or equal to zero).

The optimized objective function should minimize the dose deposited in the ATR and the OARs. Theoretically, the dose in these should be zero, although it can never actually be zero in the ATR. Consider a simplified example of two beamlets only, one with weight a and the other with weight b. The terms in the traditional optimization function for the ATR and the OAR are each of the form:

$$p(a+b)^2,$$

where p is the importance parameter of the term. The optimization searches then for the minimum:

$$\min\{(a+b)^2\},$$

The minimum is zero and it occurs for a=−b. In other words, one of the weights will be negative. This is the result from the solution of a linear system of equations.

The minimum corresponds to:

$$\frac{\partial}{\partial a}(a+b)^2 = 0$$

$$\frac{\partial}{\partial b}(a+b)^2 = 0$$

which results in a+b=0.

The current approach is then to solve instead:

$$\min\{(a+b)^2\} \text{ with the constraints } a>0, b>0.$$

This can only be solved through a numerical search. In order to address this problem, embodiments of the invention use instead a term of the form:

$$p(a^2+b^2)$$

This term cannot be zero by one beamlet having a negative intensity to cancel the other. For this term to be zero, each beamlet intensity must be zero.

The system of equations is obtained from:

$$\frac{\partial}{\partial a}(a^2+b^2) = 0$$

$$\frac{\partial}{\partial b}(a^2+b^2) = 0$$

that results in a=0 b=0 at the minimum. For a quadratic optimization function, there is only one minimum, which is the absolute minimum.

Multiple forms of objective functions satisfying the optimization conditions stated above will be described herein.

One form of a typical objective function O satisfying the optimization conditions stated above is of the form:

$$O = p_{PTV}O_{PTV} + p_{OAR}O_{OAR} + p_{ATR}O_{ATR}$$

where the $p_k$ are importance coefficients (also called importance parameters) and the objectivity terms are:

$$O_{PTV} = \sum_{x \in PTV}\left(\sum_i^{all-beamlets} w_i d_i(x) - d^{PTV}\right)^2,$$

$$O_{OAR} = \sum_{x \in OAR}\left(\sum_i^{all-beamlets} w_i d_i(x)\right)^2,$$

and $$O_{ATR} = \sum_{x \in ATR}\left(\sum_i^{all-beamlets} w_i d_i(x)\right)^2,$$

where $w_i$ is the weight of beamlet i, $d_i$ is the dose deposited at destination point x by beamlet i and $d^{PTV}$ is the dose prescribed to the PTV.

The main reason for the appearance of negative weights upon optimization of the objective function O is the fact that it is usual to require the satisfaction of two conflicting demands: on one hand it is required that $O_{ATR}=0$ and on the other hand it is necessary for radiation to pass through the ATR (and possibly OARs) to reach the PTV. A better requirement is that $O_{ATR}$ should be zero only if the weights of all the beamlets passing through the ATR are zero, as described in the simplified example above. This requirement is satisfied if instead of $O_{ATR}$ we use a new ATR term of the form:

$$\tilde{O}_{ATR} = \sum_{x \in ATR}\sum_i^{all-beamlets} w_i^2 d_i^2(x).$$

Similarly for the OAR:

$$\tilde{O}_{OAR} = \sum_{x \in OAR}\sum_i^{all-beamlets} w_i^2 d_i^2(x).$$

The PTV term in the objective function O cannot be written in this way. Accordingly, the medical personnel performing the optimization needs to set an importance parameter large enough on the ATR and OAR terms to balance the PTV term. Even small values of importance parameters for the OAR and ATR have been found to be sufficient.

Optionally, a term is added to the objective function O that replaces the unrealistic zero-limit for the beamlet weights with an equal-weight limit (which will be referred to herein as circular symmetry), which is usually the initial set of weights before optimization. This term can assume different forms, as part of a general family of symmetry terms. This term can be in one of the forms:

$$O_{SYM} = \sum_i^{all-beamlets} (w_i - 1)^2$$

or $$O_{SYM} = \sum_i^{all-beamlets} (w_i^2 - w_i)$$

or $$O_{SYM} = \sum_i^{all-beams}\left[\left(\sum_j^{\substack{all-beamlets\\inside-beam-i}} w_j\right) - 1\right]^2$$

or $$O_{SYM} = \sum_i^{all-beamlets} w_i^2$$

or $$O_{SYM} = \sum_{x \in all-contours}\sum_i^{all-beamlets} w_i^2 d_i(x)$$

or $$O_{SYM} = \sum_{\substack{x \in all-contours\\exceptPTV}}\sum_i^{all-beamlets} w_i^2 d_i(x)$$

or other forms satisfying the condition in the next section. In the following we will use, for illustration, the first form of $O_{sym}$.

With the weights normalized to:

$$\sum_i^{all-beamlets} w_i = \text{total number of beamlets},$$

$O_{SYM}$ is positive and its minimum is zero when $w_i=1$ for all i. The objective function O then becomes:

$$\tilde{O} = p_{PTV}O_{PTV} + p_{OAR}\tilde{O}_{OAR} + p_{ATR}\tilde{O}_{ATR} + p_{SYM}O_{SYM}$$

The underlying approach behind current optimization techniques is to start from zero weights and analyze the results as the weights of each beamlet are increased. As a result, searches for a minimum do not necessarily result in symmetric dose depositions, even when the system treated may have a symmetry (e.g. symmetric under a reflection). The symmetry term introduced here, in essence, starts the analysis of the weights from the opposite end: with all beams having the same weight. Given that the radiation source travels around the isocentre (i.e. the designated centroid of the form or volume) describing a circle on each slice, this requirement starts the analysis from a circularly symmetric perspective.

The circular symmetry term $O_{SYM}$ has been found to introduce a high degree of stability in the results, even when coupled with a small importance parameter $p_{SYM}$. Moreover, it tends to smooth the dose distribution within the body volume, avoiding local hot or cold spots.

This introduced symmetry term provides a significant bias against generation of negative beamlet intensities during minimization of the objective function using matrix inversion. This can be observed if, for example, all importance parameters apart from $p_{SYM}$ are zero. In such a case, the optimization of the objective function would yield a plan where all beamlets have the same unit weight. Thus, a non-zero value for $p_{SYM}$ biases the beamlet weights towards a unit weight distribution. This bias is small for small values of $p_{SYM}$ and is stronger for larger values. If one were to iteratively test and observe the beamlet weight distribution, starting with a large value of $p_{SYM}$ and decreasing it in steps, the distribution would resolve from one in which all weights are substantially the same to a distribution in which the beamlet weights are substantially optimized, while keeping all beamlet weights positive.

An advantageous effect of the symmetry term in the objective function is that, for a contour having a point or axial symmetry around the isocentre, the beamlet weight distribution (and hence dose deposit) as a function of gantry angles, will closely follow that symmetry. This ability to follow symmetries is derived in part from the large number of gantry angles which can be accommodated in the optimization method described herein and translates into an ability to provide high quality conformal dose deposit mapping for target volumes in general.

With the symmetry term included, a simplified form of the new objective function can be expressed as:

$$\tilde{O} = \sum_{k}^{\text{all organs with required dose}} p_k^{dose} O_k^{dose} + \sum_{n}^{\text{all organs without required dose}} p_n^{no-dose} \tilde{O}_n^{no-dose} + p_{sym} O_{sym}$$

where $$O_k^{dose} = \sum_{x \in organ_k} \left( \sum_{i}^{\text{all-beamlets}} w_i d_i(x) - d^{organ_k} \right)^2$$

where $d^{organ_k}$ is the dose prescribed to organ k, and $$\tilde{O}_n^{no-dose} = \sum_{x \in organ_n} \sum_{i}^{\text{all-beamlets}} w_i^2 d_i^2(x)$$

The optimal set of weights is obtained by minimizing the objective function. The minimum occurs when $$\frac{\partial O}{\partial w_j} = 0$$

for all $w_j$ or $$\frac{\partial O}{\partial w_j} = \sum_{k}^{\text{all organs with required dose}} p_k^{dose} \frac{\partial O_k^{dose}}{\partial w_j} + \sum_{n}^{\text{all organs without required dose}} p_n^{no-dose} \frac{\partial \tilde{O}_n^{no-dose}}{\partial w_j} + p_{sym} \frac{\partial O^{sym}}{\partial w_j} = 0$$

where $$\frac{\partial O_k^{dose}}{\partial w_j} = 2 \sum_{i}^{\text{allbeamlets}} w_i \left( \sum_{x \in organ_k} d_i(x) d_j(x) \right) - 2 d^{organ_k} \sum_{x \in organ_k} d_j(x),$$

$$\frac{\partial \tilde{O}_n^{no-dose}}{\partial w_j} =$$

-continued $$2 w_j \left( \sum_{x \in organ_n} d_j^2(x) \right) = 2 w_j \sum_{i}^{\text{allbeamlets}} \left[ w_i \left( \sum_{x \in organ_k} d_i(x) d_j(x) \right) \times \delta_{ij} \right]$$

and $$\frac{\partial O^{sym}}{\partial w_j} = 2 w_j - 1 = 2 \left( w_j - \frac{1}{2} \right) = 2 \left[ \left( \sum_{i}^{\text{allbeamlets}} w_i \times \delta_{ij} \right) - \frac{1}{2} \right]$$

where $\delta_{ij}$ is a unit matrix (i.e., a square array with all elements zero except for the diagonal elements that are all equal to one).

Calling now $$\alpha_{ij}^{organ_k} = \sum_{x \in organ_k} d_i(x) d_j(x)$$

and $$\beta_j^{organ_k} = d^{organ_k} \sum_{x \in organ_k} d_j(x),$$

then for each beamlet across the whole body volume:

$$\alpha_{ij} = \sum_{k}^{\substack{\text{all} \\ \text{organs} \\ \text{with} \\ \text{required} \\ \text{dose}}} p_k^{dose} \alpha_{ij}^{organ_k} + \sum_{n}^{\substack{\text{all} \\ \text{organs} \\ \text{without} \\ \text{required} \\ \text{dose}}} p_n^{no-dose} \alpha_{ij}^{organ_n} \delta_{ij} + p_{sym} \delta_{ij}$$

and $$\beta_i = \sum_{k}^{\substack{\text{all} \\ \text{organs} \\ \text{with} \\ \text{required} \\ \text{dose}}} p_k^{dose} \beta_i^{organ_k} + \frac{1}{2} p_{sym}$$

With the noted modifications to the objective function, the optimization problem for all the beamlet intensities is reduced to the solution of a linear system of equations of the form:

$$\sum_{j}^{\text{allbeamlets}} \alpha_{ij} w_j = \beta_i \qquad (1)$$

where $w_j$ is the (unknown) weight or intensity of beamlet j, $\beta_j$ is a vector (referenced herein as the beamlet dose deposit vector or array) of coefficients that depends on the dose deposited by beamlet i within the PTV, and $\alpha_{ij}$ is a matrix (referenced herein as the beamlet intersection matrix) that describes the product of the doses deposited by the intersecting pairs of beamlets i and j on all organs.

The set of optimal beamlet weights is obtained, for example, from (1) by inversion:

$$w_i = \sum_{j}^{\text{allbeamlets}} \alpha_{ij}^{-1} \beta_j$$

Thus, the solution to the (large) system of linear equations (1) can be obtained quickly and accurately by inverting the matrix $\alpha_{ij}$ using standard matrix inversion routines and summing the product of inverted matrix $\alpha_{ij}^{-1}$ with vector $\beta_j$ for each beamlet j.

The importance parameters for each region can be generalized to be region-dependent, i.e. to have different values in a region within a contour, in which case they can be the form $$p_{region_k} = \hat{p}_{region_k} q_{region_k}(x)$$

where $\hat{p}$ is the overall constant and $q(x)$ is a function of position.

In this case, the definitions of the arrays $\alpha$ and $\beta$ may be generalized by $$\hat{\alpha}_{ij}^{region_k} = \sum_{x \in region_k} q_{region_k}(x) d_i(x) d_j(x)$$

$$\hat{\beta}_j^{region_k} = d^{region_k} \sum_{x \in region_k} q_{region_k}(x) d_j(x)$$

Using these definitions, the matrix formulation of the optimization process now becomes:

$$\hat{\alpha}_{ij} = \hat{p}_{PTV} \hat{\alpha}_{ij}^{PTV} + (\hat{p}_{OAR} \hat{\alpha}_{ij}^{OAR} + \hat{p}_{ATR} \hat{\alpha}_{ij}^{ATR} + p_{sym}) \delta_{ij}$$

$$\hat{\beta}_j = \hat{p}_{PTV} \hat{\beta}_{ij}^{PTV} + p_{sym}$$

The previous linear system of equations is now $$\sum_i w_i \hat{\alpha}_{ij} = \hat{\beta}_j$$

and the optimized solution is obtained by the inversion:

$$w_i = \sum_j^{allbeamlets} \hat{\alpha}_{ij}^{-1} \hat{\beta}_j$$

If the functional dependence of the importance coefficients remains unaltered, a search of the best set of importance parameters is reduced to a search of the best set $\hat{p}_{region_k}$ in which case the arrays $\hat{\alpha}_{region_k}$ and $\hat{\beta}_{region_k}$ do not need to be recalculated. Matrices $\hat{\alpha}_{ij}$ and $\hat{\beta}_{ij}$ are obtained from matrices $\hat{\alpha}_{ij}$ and $\hat{\beta}_{ij}$ by simply setting $q_{region_k}=1$ for all regions, returning to the case in which the importance coefficient has a unique value within a contour.

The objective function O may alternatively have the form:

$$O = p_{PTV} O_{PTV} + p_{PTV}^c O_{PTV}^c + p_{OAR}^c O_{OAR}^c + p_{ATR}^c O_{ATR}^c$$

where the $p_k$ terms are importance coefficients (also called importance parameters) and the objectivity terms are as described in detail herein.

The objectivity terms that relate to the PTV are as follows:

$$O_{PTV} = \frac{1}{2} \sum_{x \in PTV} \left[ \sum_i^{allbeamlets} w_i d_i(x) - d^{PTV} \right]^2$$

$$O_{PTV}^C = \frac{1}{2} \sum_{x \in PTV} \sum_i^{allbeamlets} \left( w_i d_i(x) - \tilde{d}^{PTV}(x) \right)^2$$

where $w_i$ is the weight or intensity of beamlet i, $d_i$ is the dose deposited at destination point x by beamlet i, $d^{PTV}$ is the dose prescribed to the PTV, and $\tilde{d}^{PTV}(x)$ is the average prescribed dose per beamlet at destination point x inside the PTV. The $\tilde{d}^{PTV}(X)$ term may be expressed as:

$$\tilde{d}^{PTV}(x) = \frac{d^{PTV}}{n_b^{PTV}(x)}$$

where the $n_b^{PTV}(x)$ term is the number of beamlets passing through destination point x inside the PTV.

While the $O_{PTV}$ term is common to both embodiments of the objective function, the $O_{PTV}^C$ term (herein referred to as the PTV constraint term) is introduced in this alternative objective function. The $\tilde{d}^{PTV}(x)$ term in effect is an approximate condition for the dose distribution in the PTV that would be exact if there was no exponential decay in the beam and no inverse square law, as understood by those skilled in the art.

The underlying approach behind the PTV constraint term is to bias the actual dose deposited by an individual beamlet (i.e. $w_i d_i(x)$) towards the average dose per beamlet at a destination point within the PTV (i.e. $\tilde{d}^{PTV}(x)$), which is a positive value. This introduced $O_{PTV}^C$ term provides a significant bias against the generation of negative beamlet weights during minimization of the objective function, as the PTV constraint term has a minimum of zero, which is achieved when the product of an individual beamlet weight and the dose deposited by the individual beamlet is equal to a positive value, the average dose per beamlet at a destination point within the PTV (i.e. when $w_i d_i(x) = \tilde{d}^{PTV}(x)$).

This can be observed by a simplified example. Assume we have two beamlets (i.e. $n_b^{PTV}(x)=2$), with $d^{PTV}=20$ and $\tilde{d}^{PTV}(x)=10$. Assume the weight of each respective beamlet is $w_1=50$, $w_2=-30$, and for simplicity let $d_{1,2}(x)=1$.

Where all importance parameters apart from $p_{PTV}$ are zero, the optimization of the objective function would yield a result where the existence of a negative weight unrealistically minimizes the $O_{PTV}$ term to zero, while at the same time unrealistically having the other beamlet deposit a dose in the PTV to satisfy the prescribed dose for the PTV (i.e. $O_{PTV}=(50+(-30)-20)^2=0$). In this instance, the $O_{PTV}$ term is minimized when the collective weight of the beamlets (since $d_{1,2}(x)=1$) is equal to the prescribed dose for the PTV.

Where all importance parameters apart from $p_{PTV}^c$ are zero, the optimization of the objective function will generally not yield a result where the existence of a negative weight minimizes the $O_{PTV}^C$ term. Instead, the $O_{PTV}^C$ term is minimized when the individual beamlet weights (since $d_{1,2}(x)=1$) equal the average dose per beamlet at a destination point within the PTV, which is a positive value. In this example, the existence of a negative weight does not help minimize $O_{PTV}^C$ and instead results in a large value for the $O_{PTV}^C$ term (i.e. $O_{PTV}^C = (50-10)^2 + (-30-10)^2 = 3200$), which is undesirable for optimization purposes.

Accordingly, during optimization, a non-zero value for the importance parameter $p_{PTV}^c$ term significantly biases the actual dose deposited by an individual beamlet (i.e. $w_i d_i(x)$) towards a positive value, as in practice, the average dose per beamlet at a destination point within the PTV is not a negative value. Moreover, as the dose deposited by a beamlet is, in practice, not a negative value, then in turn the individual beamlet weights are biased towards a positive value, since otherwise the $w_i d_i(x)$ would be a negative value. As explained above, a negative value for $w_i d_i(x)$ will not generally minimize the PTV constraint term as its minimum of 0 is achieved when $w_id_i(x)$ is equal to $\tilde{d}^{PTV}(x)$, a positive value.

The objectivity term that relates to the OAR (or, more generally, one of the non-target volumes) is as follows:

$$O_{OAR}^C = \frac{1}{2} \sum_{x \in OAR} \sum_{1}^{allbeamlets} (w_i d_i(x) - \tilde{d}^{OAR}(x))^2$$

where $\tilde{d}^{OAR}(x)$ is a predetermined average dose constraint value for a destination point inside the OAR, which, for example, may be defined as the average dose per beamlet at destination point x inside the OAR, which may be expressed in the form:

$$\tilde{d}^{OAR}(x) = \frac{d^{PTV} \times c^{OAR}(\%)}{n_b^{OAR}(x)}$$

where $d^{PTV}$ is still the dose prescribed to the PTV, $n_b^{OAR}(x)$ is the number of beamlets passing through destination point x inside the OAR and $c^{OAR}(\%)$ is a predetermined percentage of the dose prescribed to the PTV that is permitted in the OAR. The predetermined average dose constraint value for the OAR expressed above is localized, as its value may change for each destination point x within the OAR. The predetermined average dose constraint value may also be a user-configurable dose-volume constraint value for the OAR.

Alternatively, $\tilde{d}^{OAR}(x)$ can expressly relate to a prescribed dose constraint for the OAR and does not have to directly factor in the dose prescribed to the PTV. The dose constraint value prescribed to the OAR in effect provides that the OAR shall not receive a higher dose then the value of the dose constraint. This alternative expression for $\tilde{d}^{OAR}(x)$ may be:

$$\tilde{d}^{OAR}(x) = \frac{d_{DHV}^{OAR}}{n_b^{OAR}(x)}$$

where $d_{DVH}^{OAR}$ is the prescribed dose constraint for the OAR and $n_b^{OAR}(x)$ is the number of beamlets passing through destination point x inside the OAR.

The purpose of using the $O_{OAR}^C$ term (herein referred to as the OAR constraint term) is to allow the objective function to take into account predetermined dose-volume constraints for the OAR, by incorporating, for example, the $\tilde{d}^{OAR}(x)$ term.

As an example, reference will be made to FIG. 9A which shows a dose-volume histogram 904 for IMRT, where the OAR volume 914 is a spine. In this example, it is particularly important to minimize the radiation delivered to the spine, as an excessive dose may result in damage to the spinal cord or nerve endings therein. In one embodiment, a dose-volume histogram, such as the dose-volume histogram 902 illustrated in FIG. 9A, may be interpreted as indicating dose-volume constraints corresponding to the non-target and target volumes.

For example, a dose-volume histogram curve, such as OAR curve 924 in the dose-volume histogram 904, may be interpreted as providing a dose-volume histogram constraint curve for the OAR. A dose-volume histogram constraint curve provides that a percentage of the OAR (ranging from 0% to 100%) should not receive more than a predetermined percentage of the dose prescribed to the PTV. In this example, the OAR curve 924 may provide that none (i.e. 0%) of the OAR volume 914 (i.e. the spine) should receive more the 40% of the dose prescribed to the PTV volume 916. In other words the $c^{OAR}(\%)$ for the OAR volume 914 is 40%, which may be incorporated into the $\tilde{d}^{OAR}(x)$ term, which is an example of a predetermined average dose constraint value. The $O_{OAR}^C$ term takes a dose-volume constraint for the OAR into account by biasing the OAR dose deposited by each beamlet passing through the OAR (i.e. $w_id_i(x)$ for each beamlet i) to a predetermined average dose constraint value, i.e. $\tilde{d}^{OAR}(x)$.

Accordingly, in one embodiment, $\tilde{d}^{OAR}(X)$ is an approximate condition for the dose distribution at a destination point x inside the OAR which satisfies a dose-volume histogram constraint curve, as expressed by $c^{OAR}(\%)$. However, in an additional embodiment, the value prescribed to $c^{OAR}(\%)$ when performing an optimization may be a lower value than that indicated by a dose-volume histogram constraint curve, if for example, a lower dose distribution inside the OAR then that required by the constraint is desired. This is particularly advantageous when OAR volumes are particularly sensitive to radiation, such as for example the spine, where an excessive dose of radiation can have extremely detrimental effects, as noted above.

The value prescribed to $c^{OAR}(\%)$ is not limited to a dose-volume histogram constraint curve, and may represent any dose-volume constraint for the OAR. Moreover, the value prescribed to $\tilde{d}^{OAR}(x)$ may be any predetermined average dose constraint value for a destination point inside the OAR, such as a user-configurable dose-volume constraint.

It can be difficult to direct a radiation beam so as to deliver the dose prescribed to the PTV without also directing some radiation towards the OAR. However, the OAR constraint term takes this difficulty into account, and instead of optimizing the OAR dose to zero (as previously done with $O_{OAR}$) the OAR dose is optimized towards a more physically realistic positive value, specifically, $\tilde{d}^{OAR}(x)$. The $O_{OAR}$ term previously described is a special case of the general OAR constraint term, specifically when $c^{OAR}(\%)$ is 0.

Furthermore, similar to the PTV constraint term, during optimization, a non-zero value for the importance parameter $p_{OAR}^c$ term provides a significant bias against the generation of negative beamlet weights, as the OAR constraint term has a minimum of 0, which is achieved when the actual dose delivered by individual beamlets passing through the OAR (i.e. $w_id_i(x)$) equals $\tilde{d}^{OAR}(x)$, which is in practice a positive value. As explained above, since the dose deposited by a beamlet is, in practice, not a negative value, then in turn the individual beamlet weights are biased towards a positive value, since otherwise the $w_id_i(x)$ term would be a negative value.

Accordingly, the OAR constraint term should be zero only if, for all beamlets passing through the OAR, the product of the weight of a beamlet passing through a destination point inside the OAR and the dose deposited by the corresponding beamlet at the destination point inside the OAR (i.e. $w_id_i(x)$) is equal to $\tilde{d}^{OAR}(x)$ which is an example of a predetermined average dose constraint value. As explained above, the appearance of negative beamlet weights will generally not minimize the OAR constraint term. The dose deposited by a beamlet ($d_i(x)$) is in practice a positive value, therefore a negative beamlet weight ($w_i$) would make the $w_id_i(x)$ term a negative value and the OAR constraint term is minimized when the $w_id_i(x)$ term is equal to the $\tilde{d}^{OAR}(x)$, a positive value. However, it has been determined that if the value of $\tilde{d}^{OAR}(x)$ is too small, negative beamlet weights may start to appear, which in effect suggests that an extremely low dose in the OAR, i.e. $\tilde{d}^{OAR}(x)$, may not be possible for the specific case under consideration.

The objectivity term that relates to the ATR (or, more generally, on of the non-target volumes) is as follows:

$$O_{ATR}^C = \frac{1}{2} \sum_{x \in ATR}^{allbeamlets} \sum_{1} (w_i d_i(x) - \tilde{d}^{ATR}(x))^2$$

where $\tilde{d}^{ATR}(x)$ is a predetermined average dose constraint value for a destination point inside the ATR, which may be defined as the average dose per beamlet at destination point x inside the ATR. The $\tilde{d}^{ATR}(x)$ term may be expressed as:

$$\tilde{d}^{ATR}(x) = \frac{d^{PTV} \times c^{ATR}(\%)}{n_b^{ATR}(x)}$$

where $d^{PTV}$ is still the dose prescribed to the PTV, $n_b^{ATR}(x)$ is the number of beamlets passing through destination point x inside the ATR and $c^{ATR}(\%)$ is a predetermined percentage of the dose prescribed to the PTV that is permitted in the ATR. The predetermined average dose constraint value for the ATR expressed above is localized, as its value may change for each destination point x within the ATR. The predetermined average dose constraint value for the ATR may also be a user-configurable dose-volume constraint value for a destination point inside the ATR.

As previously explained, the generation of negative weights is mainly due to the fact that the objective function aims to satisfy two conflicting demands: on the one hand a positive prescribed radiation dose must be delivered to the PTV and on the other hand the planned dose delivery attempts to achieve a zero dose in the ATR. Satisfying both those constraints is not possible as all radiation beams must pass through the ATR to arrive at the PTV. Accordingly, the $O_{ATR}^C$ term (herein referred to as the ATR constraint term) takes this contradictory demand into account, and instead of biasing the ATR dose to zero (as previously done with $O_{ATR}$), the ATR dose is biased towards a more physically realistic positive value, specifically, $\tilde{d}^{ATR}(x)$. Those skilled in the art will understand that the $O_{ATR}$ term previously described is a special case of the general ATR constraint term, specifically when $c^{ATR}(\%)$ is 0.

Furthermore, similar to the PTV and OAR constraint terms, during optimization, a non-zero value for the importance parameter $p_{ATR}^c$ term provides a significant bias against the generation of negative beamlet weights, as the ATR constraint term has a minimum of 0 which is achieved when the actual dose delivered by individual beamlets passing through the ATR (i.e. $w_i d_i(x)$) equals $\tilde{d}^{ATR}(x)$, which is in practice a positive value.

As explained above, the appearance of negative beamlet weights will generally not minimize the ATR constraint term. The dose deposited by a beamlet ($d_i(x)$) is in practice a positive value, therefore a negative beamlet weight ($w_i$) would make the $w_i d_i(x)$ term a negative value and the ATR constraint term is minimized when the $w_i d_i(x)$ term is equal to the $\tilde{d}^{ATR}(x)$ term, a positive value. However, it has been determined that if the value of $\tilde{d}^{ATR}(x)$ is too small, negative beamlet weights may start to appear, which in effect, suggests that an extremely low dose in the ATR, i.e. $\tilde{d}^{ATR}(x)$, may not be possible for the specific case under consideration.

Accordingly, the ATR constraint term should be zero only if, for all beamlets passing through the ATR, the product of the weight of a beamlet passing through a destination point inside the ATR and the dose deposited by the corresponding beamlet at the destination point inside the ATR (i.e. $w_i d_i(x)$) is equal to $\tilde{d}^{ATR}(x)$, which is an example of a predetermined average dose constraint value.

Similar to the OAR constraint term, the purpose of the ATR constraint term is to allow the objective function to take into account predetermined dose-volume constraints for the ATR, by incorporating the $\tilde{d}^{ATR}(x)$ term. As explained above, in one embodiment, the $c^{ATR}(\%)$ term may be used to satisfy a constraint such as may be illustrated by a dose-volume histogram constraint curve, which specifically provides that a percentage (ranging from 0% to 100%) of the ATR should not receive more than a predetermined percentage of the dose prescribed to the PTV. Accordingly, during optimization the ATR constraint term takes into account a dose-volume constraint (such as for example $c^{ATR}(\%)$) by optimizing the product of the weight of a beamlet passing through the ATR and the dose deposited by the corresponding beamlet (i.e. $w_i d_i(x)$) to a predetermined average dose constraint value, $\tilde{d}^{ATR}(x)$.

Accordingly, in one embodiment, $\tilde{d}^{ATR}(x)$ is an approximate condition for the dose distribution at a destination point x inside the ATR which satisfies a dose-volume histogram constraint, as expressed by $c^{ATR}(\%)$. However, in an additional embodiment, the value prescribed to $c^{ATR}(\%)$ when performing an optimization may be a lower value then that indicated by a dose-volume histogram constraint curve, if for example, a lower dose distribution inside the ATR than that required by the constraint is desired.

The value prescribed to $c^{ATR}(\%)$ is not limited to a dose-volume constraint provided in a dose-volume histogram constraint curve, and may represent any dose-volume constraint for the ATR. Moreover, generally the value prescribed to $\tilde{d}^{ATR}(x)$ may be any predetermined average dose constraint value for a destination point inside the ATR, such as for example, a dose-volume constraint configurable by a user.

In some embodiments, a smoothing term may be added to the alternative objective function O. The smoothing term may be an average smoothing term or a local smoothing term. In one example, an average smoothing term may be expressed as:

$$O_{MLC}^{ave} = \frac{1}{2} \sum_{k}^{allbeams} \sum_{1}^{allbeamlets\ inbeamk} (w_i \langle w \rangle_k)^2$$

where $w_i$ is the weight or intensity of beamlet i in beam k, and $\langle w \rangle_k$ is the average weight or intensity of all beamlets in beam k.

In another example, a local smoothing term may be expressed as:

$$O_{MLC}^{local} = \frac{1}{4} \sum_{k}^{allbeams} \frac{1}{N_k} \sum_{i,j}^{allbeamlets\ inbeamk} (w_i - w_j)^2$$

where $w_i$ is the weight or intensity of beamlet i, and $w_j$ is the weight or intensity of beamlet j, and i and j are adjacent beamlets in beam k.

The purpose of using the smoothing term is to provide a more uniform distribution of beamlet weights within their respective beam. This is because the smoothing term tends to smooth the weight distribution, and in turn the dose distribution, reducing the occurrence of local hot or cold spots (i.e. local minima or maxima intensity).

A non-zero value for importance parameter $p_{MLC}^{ave}$ during optimization would allow the average smoothing term $O_{MLC}^{ave}$ to bias the weight of all beamlets in beam k towards the average beamlet weight in beam k. Similarly, a non-zero value for the importance parameter $p_{MLC}^{local}$ during optimization would allow the local smoothing term $O_{MLC}^{local}$ to bias the weight of all beamlets in beam k towards the weight of an adjacent beamlet in beam k. This in effect optimizes beamlet weights to a more uniform distribution withing their respective beam, as they are biased towards either an adjacent beamlet weight or a local average weight for all beamlets in a corresponding beam.

A more uniform weight distribution is important as radiation beams are usually collimated by a multi-leaf collimator (MLC). Varying weight distributions for adjacent beamlets or beamlets within a respective beam may result in unrealizable distributions of MLC leaf sequencing positions. Accordingly, more uniform beamlet weight distributions within their corresponding beam result in more realizable MLC leaf sequencing positions.

Furthermore, similar to the PTV, OAR and ATR constraint terms, the smoothing terms generally assist in avoiding the generation of negative weights, as a non-zero term for an importance parameter associated with either smoothing term, during optimization, results in the individual beamlet weights being biased towards either the average weight of all beamlets of the respective beam or the weight of an adjacent beamlet.

Moreover, the average smoothing term $O_{MLC}^{ave}$ is positive and its minimum is zero when $w_i = \langle w \rangle_k$ for all beamlets i in beam k, as will be understood by persons skilled in the art. The local smoothing term $O_{MLC}^{local}$ is positive and its minimum is zero when $w_i = w_j$ for all beamlets i in beam k.

The smoothing terms may also be scaled by a corresponding importance parameter. A higher value for a smoothing term importance parameter allows the smoothing term to have a greater importance and influence during the optimization of the objective function. After an optimization yields a planned dose distribution, the smoothing term importance parameter may be adjusted to refine the planned dose distribution if, for example, a more uniform distribution is desired in order to suit MLC leaf sequencing or to accommodate other physical constraints imposed by the radiation therapy delivery system.

An alternative form of the objective function O, which optionally includes both these smoothing terms, then becomes:

$$\tilde{O} = p_{PTV}O_{PTV} + p_{PTV}^c O_{PTV}^c + p_{OAR}O_{OAR}^c + p_{ATR}^c O_{ATR}^c + p_{MLC}^{ave}O_{MLC}^{ave} + p_{MLC}^{local}O_{MLC}^{local}$$

Again, the optimal set of weights is obtained by minimizing the objective function $\tilde{O}$. Similarly, the minimum occurs when:

$$\frac{\partial \tilde{O}}{\partial w_j} = 0$$

for all $w_j$ where $$\frac{\partial O_{PTV}}{\partial w_j} = \sum_i^{allbeamlets} w_i \left( \sum_{x \in PTV} d_i(x)d_i(x) \right) - d^{PTV} \sum_{x \in PTV} d_j(x)$$

$$\frac{\partial O_{PTV}^c}{\partial w_j} = w_j \left( \sum_{x \in PTV} d_j^2(x) \right) - \sum_{x \in PTV} \tilde{d}^{PTV}(x)d_j(x) =$$

$$w_j \sum_i^{allbeamlets} \left[ w_i \left( \sum_{x \in PTV} d_i(x)d_j(x) \right) \times \delta_{ij} \right] - \sum_{x \in PTV} \tilde{d}^{PTV}(x)d_j(x)$$

$$\frac{\partial O_{OAR}^c}{\partial w_j} = w_j \left( \sum_{x \in OAR} d_j^2(x) \right) - \sum_{x \in OAR} \tilde{d}^{OAR}(x)d_j(x) =$$

$$w_j \sum_i^{allbeamlets} \left[ w_i \left( \sum_{x \in OAR} d_i(x)d_j(x) \right) \times \delta_{ij} \right] - \sum_{x \in OAR} \tilde{d}^{PTV}(x)d_j(x)$$

$$\frac{\partial O_{ATR}^c}{\partial w_j} = w_j \left( \sum_{x \in ATR} d_j^2(x) \right) - \sum_{x \in ATR} \tilde{d}^{ATR}(x)d_j(x) =$$

$$w_j \sum_i^{allbeamlets} \left[ w_i \left( \sum_{x \in ATR} d_i(x)d_j(x) \right) \times \delta_{ij} \right] - \sum_{x \in ATR} \tilde{d}^{ATR}(x)d_j(x)$$

$$\frac{\partial O_{MLC}^{ave}}{\partial w_j} = w_j - \langle w \rangle_k = \sum_i^{allbeamlets} w_i \delta_{ij} - \langle w \rangle_k$$

$$\frac{\partial O_{MLC}^{local}}{\partial w_j} = \sum_i^{allbeamlets} w_i \left( \delta_{ij} - \frac{1}{N_k} \right)$$

where $\delta_{ij}$ is a unit matrix (i.e., a square array with all elements zero except for the diagonal elements that are all equal to one).

Calling now $$a_{PTVi,j} = \sum_{x \in PTV} d_i(x)d_j(x)$$

$$a_{PTVi,j}^c = \sum_{x \in PTV} d_i(x)d_j(x)\delta_{ij}$$

$$a_{OARi,j}^c = \sum_{x \in OAR} d_i(x)d_j(x)\delta_{ij}$$

$$a_{ATRi,j}^c = \sum_{x \in ATR} d_i(x)d_j(x)\delta_{ij}$$

$$a_{MLCi,j}^{ave} = \delta_{ij}$$

$$a_{MLCi,j}^{local} = \delta_{ij} - \frac{1}{N_k}$$

and $$\beta_{PTVi} = d^{PTV} \sum_{x \in PTV} d_i(x)$$

$$\beta_{PTVi}^c = \sum_{x \in PTV} d_i(x)\tilde{d}^{PTV}(x)$$

$$\beta_{OARi}^c = \sum_{x \in OAR} d_i(x)\tilde{d}^{OAR}(x)$$

$$\beta_{ATRi}^c = \sum_{x \in ATR} d_i(x)\tilde{d}^{ATR}(x)$$

$$\beta_{MLCi}^{ave} = \langle w \rangle_k$$

$$\beta_{MLCi}^{local} = 0$$

Then for each beamlet across the whole body volume:

$$\alpha_{ij} = p_{PTV}\alpha_{PTV} + p_{PTV}{}^c\alpha_{PTV}{}^c + p_{OAR}{}^c\alpha_{OAR}{}^c + p_{ATR}{}^c\alpha_{ATR}{}^c + p_{MLC}{}^{ave}\alpha_{MLC}{}^{ave} + p_{MLC}{}^{local}\alpha_{MLC}{}^{local}$$

$$\beta_{ij} = p_{PTV}\beta_{PTV} + p_{PTV}{}^c\beta_{PTV}{}^c + p_{OAR}{}^c\beta_{OAR}{}^c + p_{ATR}{}^c\beta_{ATR}{}^c + p_{MLC}{}^{ave}\beta_{MLC}{}^{ave}$$

Making these noted modifications to the alternative objective function $\tilde{O}$, the optimization problem for all beamlets intensities is similarly reduced to the solution of a linear system of equations of the form:

$$\sum_{j}^{allbeamlets} \alpha_{ij} w_j = \beta_i \quad (1)$$

where $w_j$ is the (unknown) weight or intensity of beamlet j, $\beta_j$ continues to be referred to as the beamlet dose deposit vector or array and $\alpha_{ij}$ continues to be referred to as the beamlet intersection matrix.

The set of optimal beamlet weights is obtained, for example, from (1) by inversion:

$$w_i = \sum_{j}^{allbeamlets} \alpha_{ij}^{-1} \beta_j$$

The importance parameters for each region of this alternative objective function may also be generalized to be region-dependent, as previously described above. That is, the importance parameters can have different values in a region within a contour, and again may take the form:

$$p_{region_k} = \hat{p}_{region_k} q_{region_k}(x)$$

where $\hat{p}$ is the overall constant and $q(x)$ is a function of position.

Turning now to the drawings, FIG. 1 is a block diagram illustrating an optimization process 100 according to embodiments of the invention. The optimization process 100 involves obtaining scanned input data 110 from a scanning apparatus which outputs a series of scans, for example such as computed tomography (CT) scans. This scanned input data includes a series of "slices" through the body. Each of these slices shows a part of the tumor volume in cross-section, together with the remaining body volumes, including any organs at risk. When these slices are aggregated as a series of parallel slices, a three-dimensional picture of the target tumor volume and other body volumes can be obtained. Accordingly, the input data 110 includes data concerning a number of such parallel slices, sufficient to describe the body volume, including the PTV, to which radiation will be directed. The input data 110 may be in the Dicom RT standard file format (including standardized radiation therapy-specific data objects), which can be generated by most CT scanning systems or other treatment planning systems. Further details of the Dicom RT standard can be obtained from the National Electrical Manufacturers Association (NEMA).

The input data 110 is received by an optimization module 120, which processes this input data, as described further in relation to FIGS. 2 to 7. Once the optimization module 120 has processed the input data 110, an output file 130 of the optimized beamlet intensities is generated and output to a radiation dose delivery apparatus, such as a medical linear accelerator, through a suitable Dicom RT protocol. The radiation therapy can then be delivered according to the optimized dose delivery.

Output file 130 is formatted so as to provide sequencing data for mapping the optimized beamlet intensities to the leafs of a multi-leaf collimator. This is done according to existing leaf sequencing algorithms.

The scan data 110 can be stored (e.g., in memory 20, shown in FIG. 8) and used to perform several dose optimizations over a period of time, as the optimization process facilitates adaptive adjustment of dose delivery planning based on different user input requirements.

Optimization module 120 is comprised of a series of computer program instructions aggregated to form a software program executable by a computer system (such as computer system 12 in FIG. 8, described later). Optimization module 120 is configured to receive the scan data input 110 in a known file format (e.g., Dicom RT) and to provide the optimized beamlet intensities in output file 130 in a corresponding known file format.

Optimization module 120 executes a number of sequential steps, grouped as several sets of steps, which are referred to as subprocesses, as part of the overall optimization process 100. These subprocesses include organ and contour digitization 200, beam and beamlet setup 300, dose calculation 400, pre-optimization calculation 500, beamlet optimization 600 and results and statistics generation 700. These subprocesses are described in further detail below, with reference to FIGS. 2 to 7.

Figure 2:
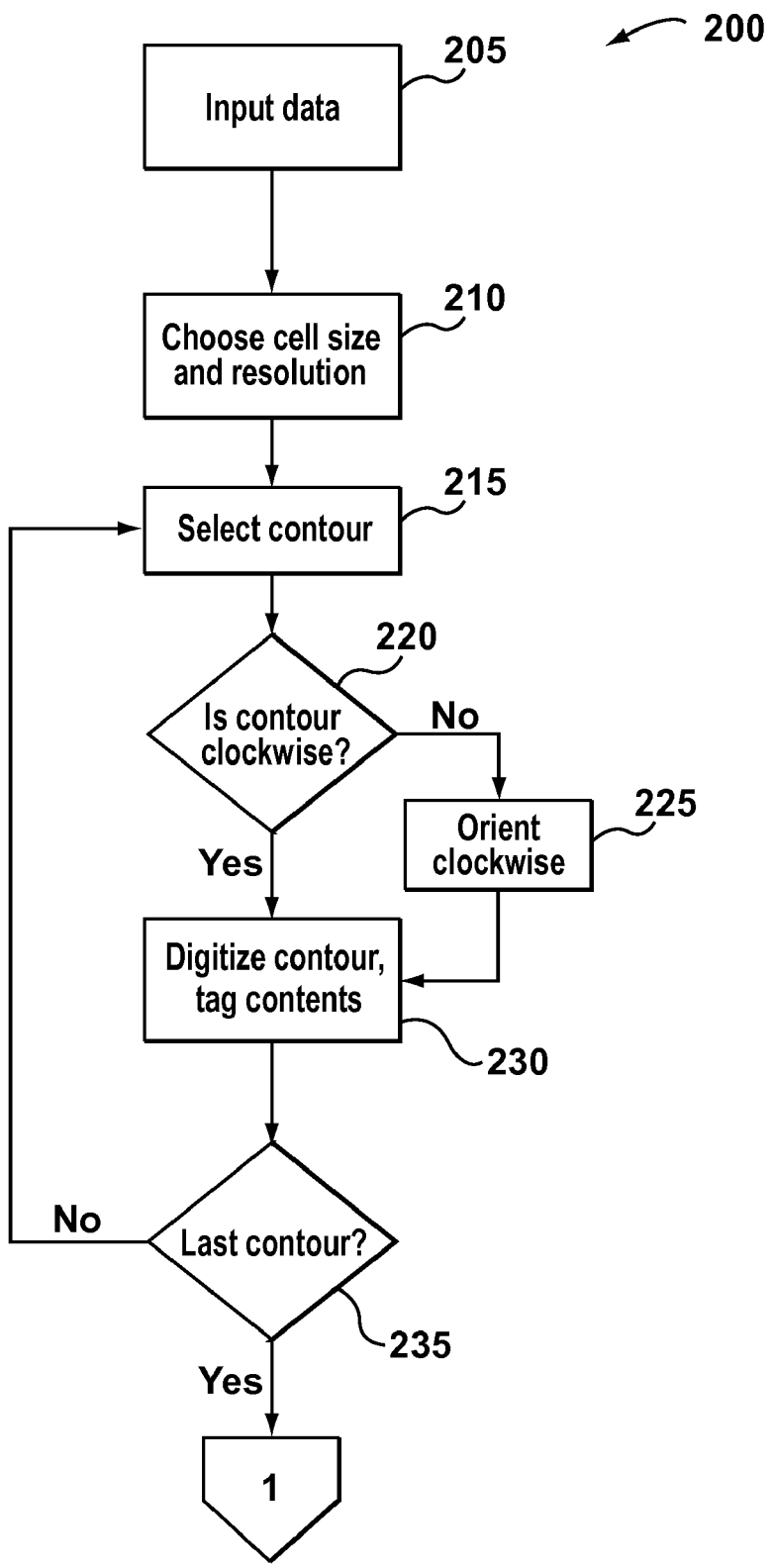
FIG. 2 is a flowchart of an organ and contour digitization sub-process of the overall process shown in FIG. 1.

Referring now to FIG. 2, organ and contour digitization subprocess 200 is described in further detail. Organ and contour digitization subprocess 200 handles the input of contour data from the CT scans and digitizes the contours so as to map them onto an underlying grid of cells to which all parts of the body volume shown in the CT scan are mapped. Subprocess 200 establishes a main array for storing data for all of the cells in the body for each CT slice. Subsets of the elements of the main array are also stored, corresponding to all of the contours within the body, such as the PTV and OAR.

At step 205, the input data 110 is received as input to the optimization module 120. The input data 110 received in this respect includes information including, for example, the treatment type (e.g. Tomotherapy, IMRT) to be performed, the required dose to be deposited within the PTV, the dose-volume constraints and the CT scans, including organ contours, determined by the radiation oncologist. The dose-volume constraints indicate the maximum or minimum radiation dose to be delivered to a particular volume. For example, for an organ at risk such as the spine, a constraint may be provided such that no more than 45 Gy of radiation dose should be received in any part of the OAR volume.

As explained above, a dose-volume histogram may be interpreted as illustrating dose-volume constraints. Specifically, the dose-volume histogram curve may be interpreted as being a dose-volume constraint curve, which provides that a percentage of a non-target volume should not receive more than a predetermined percentage of the dose prescribed to the PTV. For example, in FIG. 9A, the dose-volume histogram 902, the OAR curve 924 may be interpreted as a dose-volume constraint curve of OAR volume 914. The OAR curve 924 provides that none of the OAR volume 914 receives more than 40% of the dose. This dose-volume constraint may be incorporated into an objective function term, such as for example by setting $c^{OAR}(\%)$ equal to 40%.

Accordingly, any dose-volume constraint(s) provided by a dose-volume constraint curve, as illustrated by a dose-volume histogram, may be received as input data at step 205. A received dose-volume constraint may be incorporated into the objective function terms, such as for example $c^{OAR}$(%) and $c^{ATR}$(%). Moreover, a dose-volume constraint will generally correspond to a predetermined average dose constraint value, which may be received as input data at step 205 in other forms besides a dose-volume constraint curve. The predetermined average dose constraint values embodiments expressed as the $\tilde{d}^{OAR}$(x) term and $\tilde{d}^{OAR}$(x) are localized, as their value may change for each destination point x within the respective non-target volumes, OAR and ATR.

The predetermined average dose constraint value may also be user-configurable, such as a constant dose-volume constraint value configured by a user. A user configurable constant dose-volume constraint may also be localized for each destination point x within the respective non-target volumes. The predetermined average dose constraint value may also be a lower value than that indicated by a dose-volume constraint if a lower dose than that prescribed to the respective non-target portion is desired, as explained above.

Once the input data 110 is received at step 205, supervising medical personnel may choose, at step 210, the grid cell size and resolution to be used for optimizing the radiation dose delivery. This information is then used to generate a discretized grid having cells of the chosen size. For each CT scan, all organs, contours and beams are mapped onto a single main array representing grid cells of the chosen spatial size within the body volume. Arrays representing cells with each organ contour, beam and beamlet are subsets of this main array. Each element of each array includes the grid coordinates of the corresponding cell in the grid. A typical cell size employed by embodiments of the invention may be 1 mm square in the plane of each slice.

The properties of an organ are assumed to be uniform within each cell. Within the descretized grid, beam propagation is calculated with an accuracy given by the resolution, which is usually about 1.25 times the width (which equals the height) of each cell.

Importantly, the resolution is set greater than the cell size so that each beamlet always traverses at least the center of one cell in the grid at each depth level of its propagation. This condition produces beamlets that are more regular in shape and avoids the beamlets being discontinuous with adjacent beamlets. Within each step and within a width equal to the resolution, the beam properties are assumed to be uniform.

Because of the higher computational efficiency enabled by embodiments of the invention, more data can be handled by the optimization process 100 and a relatively high resolution and small cell size can be achieved for the cells of the PTV, OAR and ATR volumes, leading to a more optimized treatment plan for the patient.

At step 215, a contour of the PTV is retrieved from the Dicom RT input data 110. At step 220, the contour is checked for clockwise or counter-clockwise orientation. If the points of the contour are in a counter-clockwise order, the order of those points is reversed so as to be clockwise at step 225. If the points of the contour are in a clockwise order, the contour is digitized so as to interpolate a continuous contour outline from contour points provided by the radiation oncologist and the cells within the contour are tagged and saved as such, at step 230.

The method for determining the orientation of the contour is as follows. Each slice of each organ is represented by a two-dimensional contour in the plane of that slice. Here we refer to the two-dimensional contours in a specific slice. For each contour, the input data specifies a set of points or vertices (e.g. x-y coordinates) that outline that contour. These vertices are generated by the radiation oncologist on the basis of CT scan images. In order to be able to find which points are inside or outside that contour, it is necessary to first find out if the set of vertices follows a clockwise or anticlockwise direction.

Assuming a set of orthogonal axes defined in the plane of the slice:

1) Find vertex A: the topmost vertex in the contour.
2) Find vertex C: the bottom vertex in the contour.
3) Find vertex B: the rightmost vertex in the contour that is neither A or C.
4) Find vertex D: the leftmost vertex in the contour that is neither A or C.

Given that the contour encloses a finite area, at least three of the above vertices must be distinct. If the contour is in the clockwise direction, then any three distinct vertices of the above must be in the order A-B-C-D (or any cycle of this order, such as D-A-B-C). If it is not, then the contour is determined to be in an anticlockwise orientation and the order of the elements of the contour array is inverted to assume clockwise order.

After step 225 or 220, digitizing is performed at step 230, starting from the topmost vertex and proceeding clockwise to join each consecutive pair of vertices by lines. The area inside the contour is effectively divided into horizontal lines, each starting at the left boundary and ending at the right boundary. As these lines are drawn between vertices, the lines are digitized into cells or "pixels" which are inserted in the main array into which all contours are digitized.

In broad terms:
1) If the line is drawn in a direction going downwards, then each pixel on that line is a right boundary of the horizontal line at the height of the pixel.
2) If the line is drawn in a direction going upwards, then each pixel on that line is a left boundary of the horizontal line at the height of the pixel.
3) The position of all left and right boundaries for each line at each height within a contour is stored in memory.
4) After the boundary has been completely digitized, all of the cells are labeled in each horizontal line between the saved left and right boundaries as belonging to the surface enclosed by the relevant contour.

At step 235, it is determined whether the last contour has been digitized, Steps 215 to 235 are repeated for each contour and for each organ volume (eg. OAR, ATR, PTV). Once the last contour has been digitized, organ and contour digitization subprocess 200 feeds into beam and beamlet setup subprocess 300 at step 305, as indicated by reference indicator 1 in FIGS. 2 and 3.

Figure 3:
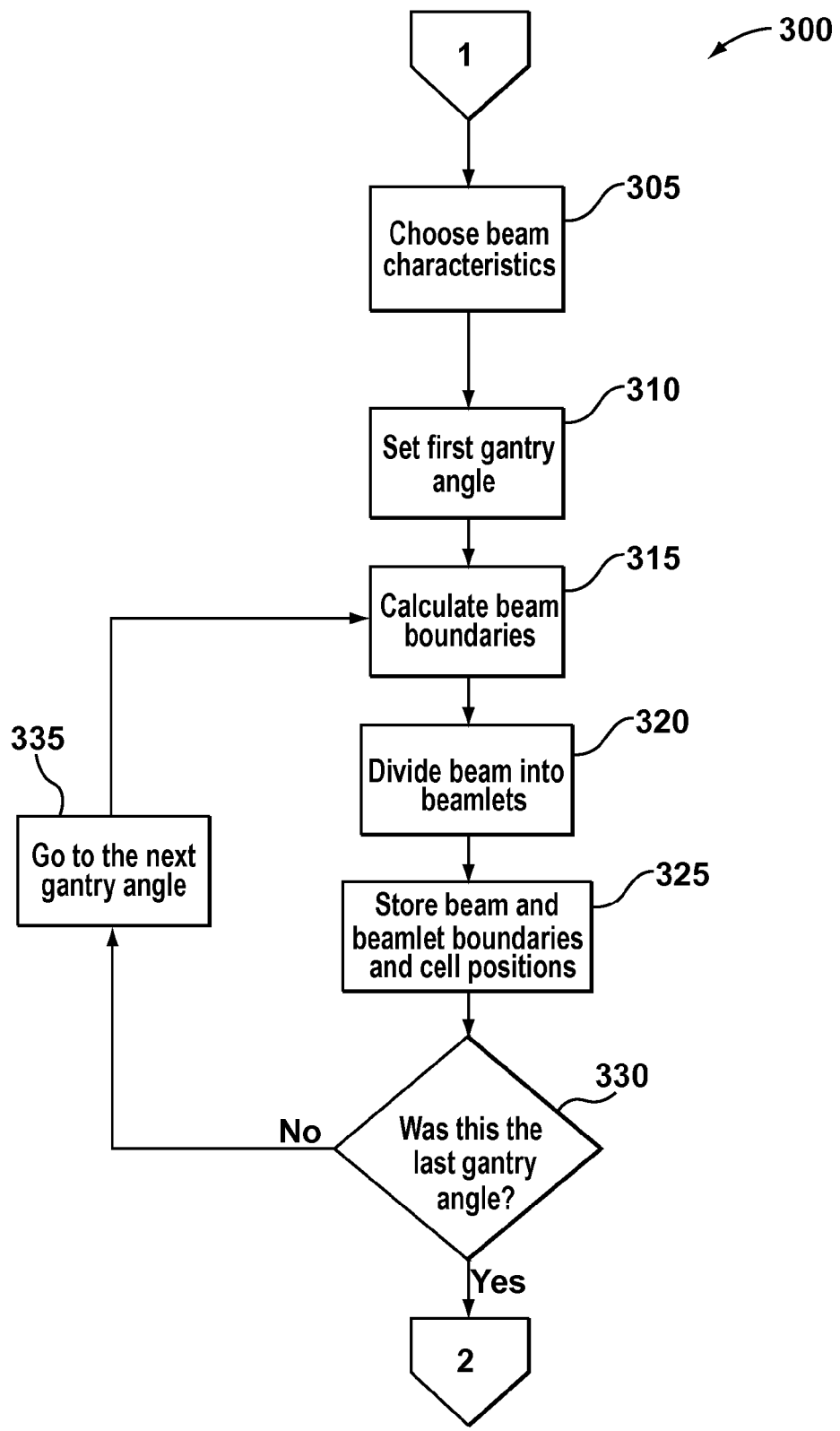
FIG. 3 is a flowchart of a beams and beamlets set-up sub-process of the process shown in FIG. 1.

Referring now to FIG. 3, beam and beamlet setup subprocess 300 is described. Beam and beamlet setup subprocess 300 determines the boundaries of each beam as projected from each different angle toward the PTV. Subprocess 300 divides the beams into beamlets, calculates the beamlet boundaries and determines which cells are inside each beamlet for each beam.

Subprocess 300 begins with data input from the user (i.e. medical personnel planning the optimized dose delivery) as to the desired radiation beam characteristics, at step 305. For example, for IMRT, multiple beams (for example, up to 51) may be specified at various angles relative to the PTV isocentre. At this step, the user also inputs beam setup information, such as the distance between the radiation source and the PTV isocentre. For Helical Tomotherapy, step 305 commonly involves choosing 51 beams at equally spaced angles, with beamlets separated by about 6.25 mm at the PTV isocentre.

For radiation therapy, the radiation beams are typically delivered to a patient lying on a bed while a gantry carrying a radiation beam emitter moves around the patient. The gantry can be positioned at numerous different angles, depending on the dose delivery plan developed by the radiation oncologist and the limitations of the radiation delivery apparatus. For IMRT, the chosen gantry angles can be along a circular arc around the patient in a single plane or in multiple intersecting planes, treating all tumor slices simultaneously, one gantry angle at a time. For Tomotherapy, each slice is treated from set gantry angles along a predetermined circular or helical arc.

Once the beam characteristics are chosen at step 305, the first of the predetermined gantry angles is set at step 310. The beam boundaries are then calculated at step 315, so as to only coincide with the outer-most edges of the PTV contour, based on the beam setup information and PTV contour data.

At each gantry angle, the position and width of the beam is calculated in order to fully cover the PTV as seen by the beam source from the radiation beam emitter.

Once the planned beam boundaries are determined at step 315, the beam is divided into beamlets at step 320. The number of beamlets within each beam will depend on the tumor-shape, gantry angle, equipment limitations, beam boundaries and previously specified resolution. Once the number of planned beamlets is determined, the positions of each of the leafs in the multi-leaf collimator are calculated for the beam from the selected gantry angle. The number of planned beamlets for each beam may be stored for later reference.

At step 325, for each beam and beamlet, the cells within each organ and contour through which each beam and beamlet would pass are stored. This allows quick calculation of beam statistics for each beam, as well as quick calculation of the optimization arrays for the beamlet intensities. In particular, this allows for the quick calculation of the number of beamlets passing through each cell within each organ and contour.

At step 330, subprocess 300 checks whether the last of the predetermined gantry angles has been selected, and if not, the next gantry angle is selected at step 335. Steps 315 to 325 are repeated for each gantry angle chosen at step 335.

Figure 4:
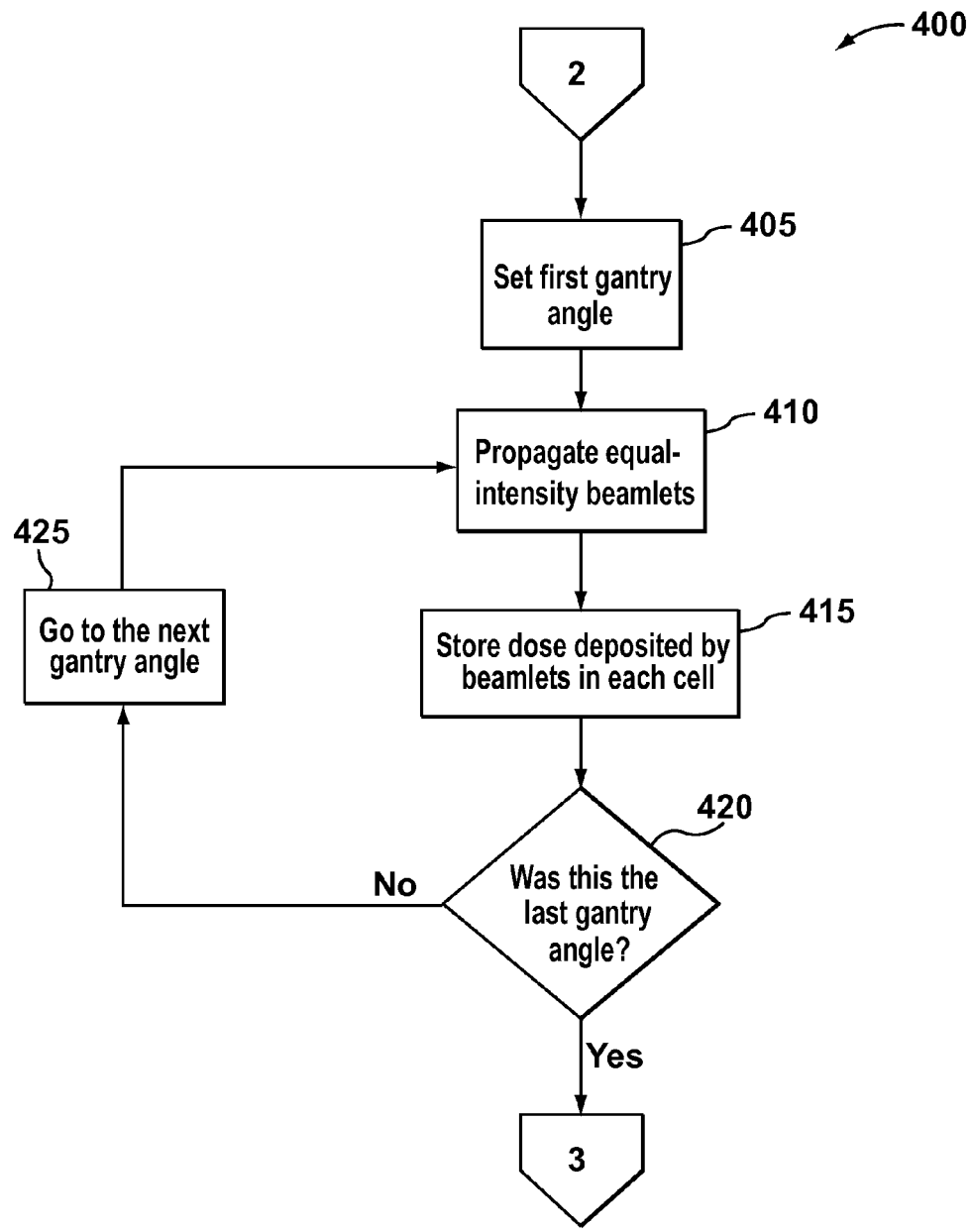
FIG. 4 is a flowchart of a dose calculations sub-process of the process shown in FIG. 1.

After the last gantry angle has been processed at step 330, subprocess 300 feeds into dose calculation subprocess 400, beginning at step 405, as indicated by reference indicator 2 in FIGS. 3 and 4.

Referring now to FIG. 4, dose calculation subprocess 400 is described. Dose calculation subprocess 400 simulates the propagation of each beamlet toward the PTV so as to determine the amount of radiation energy which would be deposited by each beamlet in each cell of each organ, based on the previously determined beam and beamlet setup. The determined dose deposit in each cell is then stored for later reference.

At step 405, the first gantry angle is selected from which beamlets are to be propagated. At step 410, equal intensity beamlets are propagated (as a simulation for planning calculation purposes only) according to the beam and beamlet setup determined in subprocess 300. In some embodiments, the equal intensity beamlets propagated at step 410 have a default normalized weighting of 1. In other embodiments, the default normalized weighting may be another non-zero positive value, so long as it is the same for all beamlets.

For radiation therapy planning calculations, the way in which each beamlet of each beam propagates through tissue and deposits energy in each cell is calculated as follows. For the purpose of calculating beamlet propagation, each (actual) beamlet is (computationally) divided into narrower sub-beamlets, termed here "elementary propagators". The width of each of these elementary propagators (at the isocentre) is equal to the resolution (approximately 1.25 times the linear cell dimension).

The energy deposit during propagation of each elementary propagator is calculated (according to a known formula) in small steps in the direction of propagation according to the resolution. The elementary propagator is divided or resolved along its length into small trapezoids (due to divergence of the beamlets from the emitter) of linear dimension equal to the resolution (i.e. slightly larger than the linear dimension of the cells in the underlying grid). Although the linear dimension (i.e., the distance between the parallel sides) of each trapezoid is uniform, each succeeding trapezoid is slightly wider than the last, so that the trapezoids are non-uniform in size.

When the center of a cell (in the main underlying grid) lies inside one of these small trapezoids, the elementary propagator is determined to deposit energy in that cell. By making the resolution slightly larger than the linear dimension of a cell, as the elementary propagator propagates, every single trapezoid into which it is divided can be considered to deposit energy into at least one cell, thus making the elementary propagator continuous and not fragmented.

The proportion of the resolution to the cell width may vary, depending on requirements, but is preferably between 1 and 2 times the cell width.

At step 415, the dose to be deposited in each cell by the propagated beamlets is stored for each cell of each organ or body volume affected by the beamlets of the beam at the selected gantry angle.

Dose calculation subprocess 400 checks at step 420 whether the selected gantry angle is the last angle at which simulated beamlet intensities are to be propagated and, if it is not, the next gantry angle is selected at step 425 and steps 410 and 415 are repeated until the last gantry angle has been simulated.

The planned beamlet intensities stored as part of subprocess 400 are used to calculate the dose which would be deposited by each beamlet in the beam at the selected gantry angle for each cell at each volume affected by the beamlets. In embodiments that use the average smoothing term, the planned beamlet intensities stored as part of subprocess 400 are also used to calculate the average weight per beamlet, <w>. The dose which would be deposited by each beamlet is calculated by propagating several elementary propagators of radiation per beamlet (as described above), each propagator being of equal width (at the isocentre) to the resolution. This calculation is performed according to existing dose deposition formulae. In storage step 415, the arrays of the cell-by-cell dose deposit data of all beamlets for all organs are stored (e.g. in RAM) for later use without recalculation.

Figure 5:
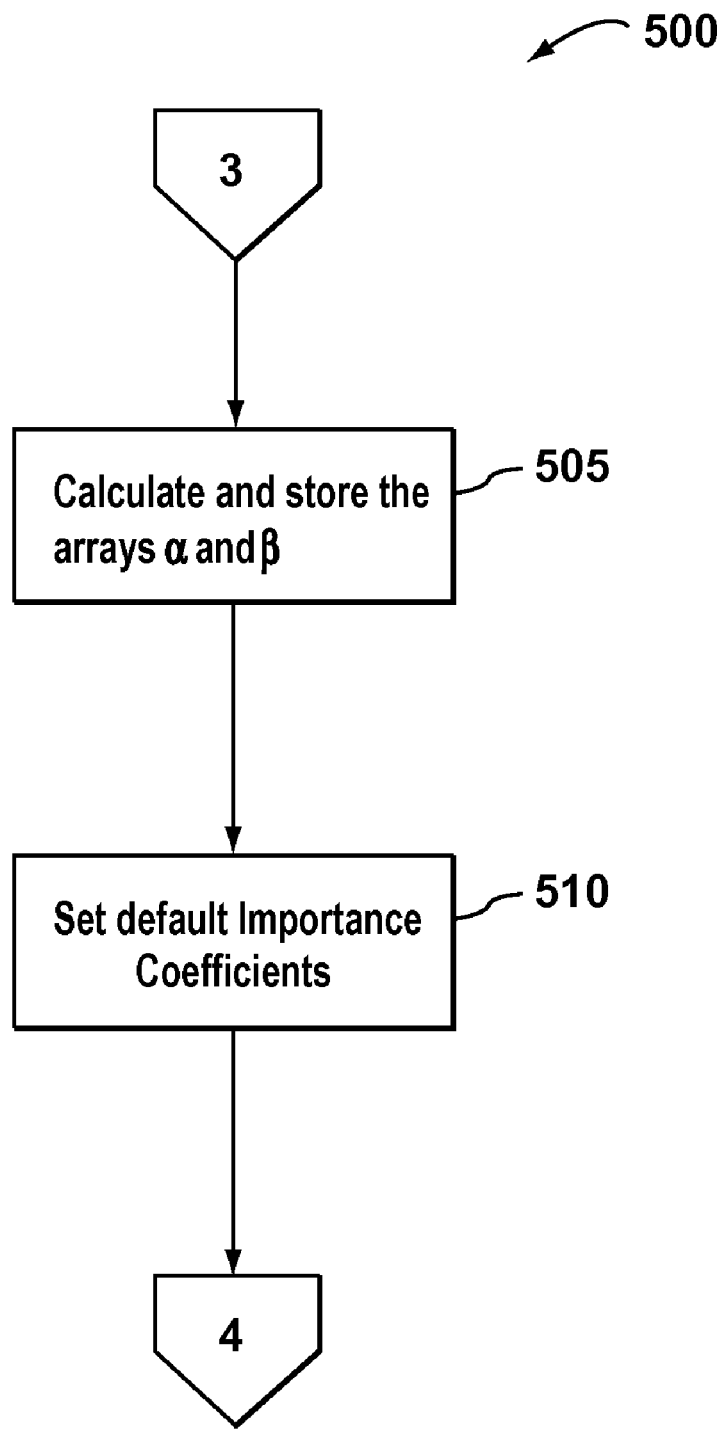
FIG. 5 is a flowchart of a pre-optimization calculations sub-process of the process shown in FIG. 1.

Dose calculation subprocess 400 feeds into pre-optimization calculation subprocess 500 in FIG. 5. Reference indicator 3 in FIGS. 4 and 5 joins the respective flowcharts in this regard.

Referring now to FIG. 5, pre-optimization calculation subprocess 500 is described. Pre-optimization calculation subprocess 500 calculates and stores the matrices and arrays of dose deposit data in each cell for each beamlet and for intersecting beamlets, in order to perform the optimization calculations.

Subprocess 500 begins with step 505, at which dose deposition coefficient arrays $\beta$ and beamlet intersection matrices $\alpha$ for all organs and contours are calculated and stored.

In embodiments that use the first described objective function that incorporates the optional symmetry term, the individual terms $\alpha$ and $\beta$ for all organs and contours are referred to as $\alpha^{organ}$ and $\beta^{organ}$, where each matrix $\alpha^{organ}$ comprises elements that are the products of the doses deposited by intersecting pairs of beamlets (i.e. from different gantry angles) across all cells in an organ (i.e. PTV, ATR or OAR). Array $\beta^{organ}$ is a vector of coefficients of the dose to be deposited by each beamlet within the cells of each organ.

For each organ, k, the matrix $\alpha^{organ}$ has elements $\alpha_{ij}^{organ_k}$ labeled by the indices i and j, determined according to the expression:

$$\alpha_{ij}^{organ_k} = \sum_{x \in organ_k} d_i(x) d_j(x)$$

where the summation runs over all points x inside organ k and $d_i(x)$ and $d_j(x)$ are the doses deposited at point x by unit-weight beamlets i and j, respectively. The terms of this matrix are quickly calculated from the arrays stored in fast memory (RAM) for the unit weight beamlets in step 415.

In embodiments that use the later described objective function with the constraint terms, the individual terms α and β for all organs and contours are individually referred to by their corresponding organ or contour, as listed below, and are determined according to the provided expressions:

$$a_{PTV,ij} = \sum_{x \in PTV} d_i(x) d_j(x)$$

$$a_{PTV,ij}^c = \sum_{x \in PTV} d_i(x) d_j(x) \delta_{ij}$$

$$a_{OAR,ij}^c = \sum_{x \in OAR} d_i(x) d_j(x) \delta_{ij}$$

$$a_{ATR,ij}^c = \sum_{x \in ATR} d_i(x) d_j(x) \delta_{ij}$$

$$a_{MLC,ij}^{ave} = \delta_{ij}$$

$$a_{MLC,ij}^{local} = \delta_{ij} - \frac{1}{N_k}$$

and $$\beta_{PTV,i} = d^{PTV} \sum_{x \in PTV} d_i(x)$$

$$\beta_{PTV,i}^c = \sum_{x \in PTV} d_i(x) \bar{d}^{PTV}(x)$$

$$\beta_{OAR,i}^c = \sum_{x \in OAR} d_i(x) \bar{d}^{OAR}(x)$$

$$\beta_{ATR,i}^c = \sum_{x \in ATR} d_i(x) \bar{d}^{ATR}(x)$$

$$\beta_{MLC,i}^{ave} = \langle w \rangle_k$$

$$\beta_{MCLC,i}^{local} = 0$$

As part of step 505, for all embodiments, the arrays and matrices for each beamlet propagated within each organ are stored in memory (e.g. RAM) for later quick retrieval during the optimization calculations. The calculations at step 505 are performed only once for the initial set of equal intensity beamlets.

At step 510, default importance coefficients for the objective function are set. These default coefficients are set according to previous experience with appropriate weighting. These coefficients are used to achieve a workable optimization of the objective function Õ. The medical physicist or other medical personnel performing the optimization may choose the default coefficients and may alter these later as part of beamlet optimization subprocess 600.

In embodiments that use the first described objective function with the optional symmetry term, typical default values for the importance parameters are, for example, $p_{PTV}=40$; $p_{OAR}=28$; $p_{ATR}=1$; and $p_{SYM}=1$. If a better conformal dose deposit within the PTV is needed, then $p_{PTV}$ is increased, for example to 100 or more. Similarly, the values for $p_{OAR}$ and $p_{ATR}$ are adjusted to suit radiation therapy planning requirements. If the system of contours is such that with these parameters or with the modified parameters the conditions on the PTV or the OAR are excessively demanding and one or more negative beamlet weights are detected, then one or both of $P_{ATR}$ and $p_{SYM}$ can be increased, typically to a value like 2 or 3.

Figure 6:
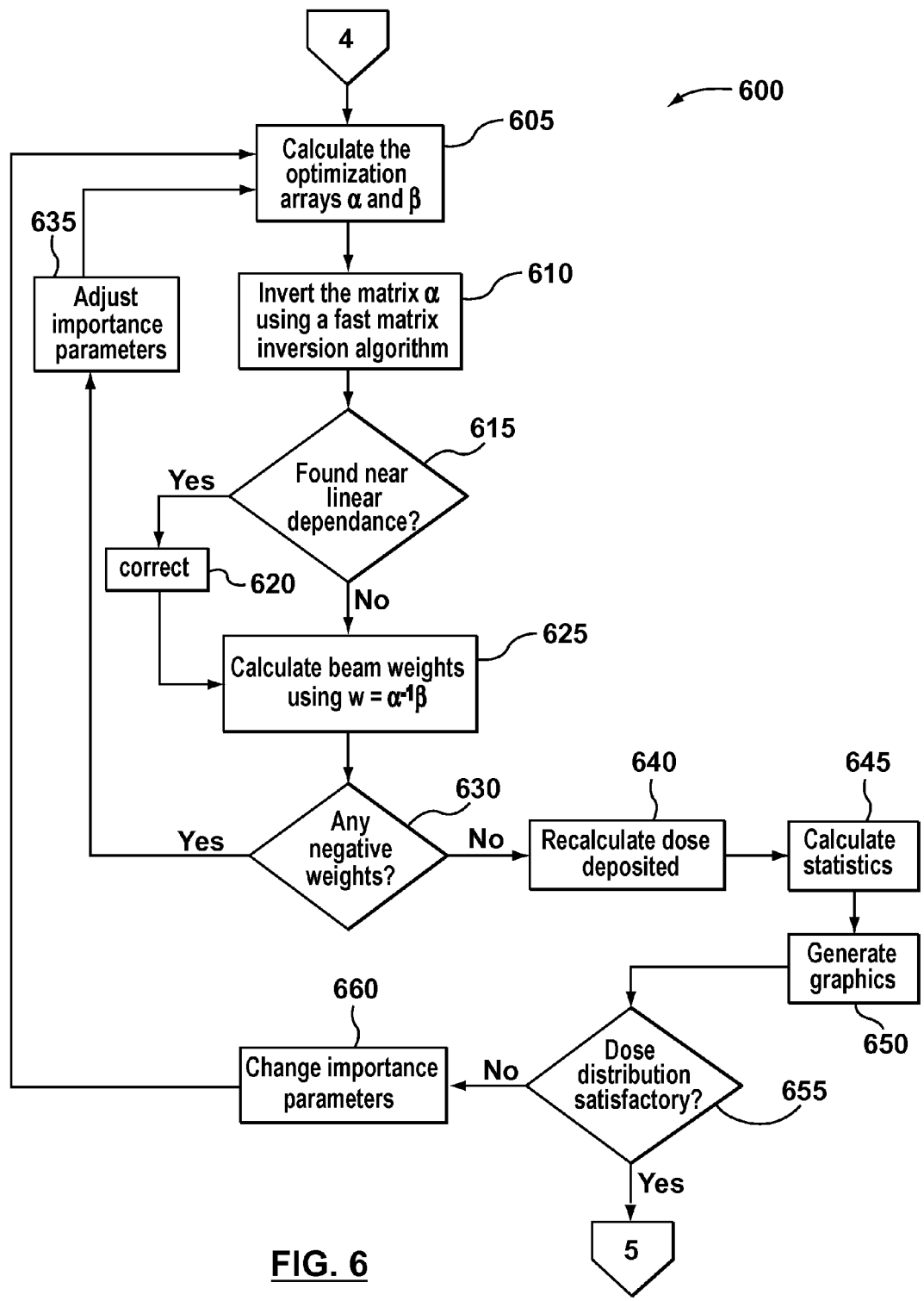
FIG. 6 is a flowchart of a beamlets optimization sub-process of the process shown in FIG. 1.

After pre-optimization calculation subprocess 500, step 510 feeds into step 605 in beamlet optimization subprocess 600. FIGS. 5 and 6 are linked by reference indicator 4 in this regard.

Referring now to FIG. 6, beamlet optimization subprocess 600 is described. Beamlet optimization subprocess 600 performs the optimization calculations by matrix inversion of the beamlet intersection matrix and determines the optimal beamlet weights according to the solution of a system of linear equations. Beamlet optimization subprocess 600 further determines the planned dose distribution among all contours and generates graphical outputs of the dose distribution.

Subprocess 600 begins with step 605, at which the overall optimization matrix $\alpha_{ij}$ and array $\beta_i$ are calculated according to the precalculated arrays and matrices for the organs and beamlets, taking into account the predetermined importance coefficients.

In one embodiment, matrix $\alpha_{ij}$ and array $\beta_i$ are calculated for each beamlet by the simple expressions:

$$\beta_i = \sum_k^{allPTV} p^{PTV_k} \beta_{iPTV_k}^{PTV_k} + \frac{1}{2} p_{sym}$$

and $$\alpha_{ij} = \sum_k^{allPTV} p^{PTV_k} \alpha_{ij}^{PTV_k} + \sum_k^{allOAR} p^{OAR_k} \alpha_{ij}^{OAR_k} \delta_{ij} + \sum_k^{allATR} p^{ATR_k} \alpha_{ij}^{ATR_k} \delta_{ij} + p_{sym} \delta_{ij}$$

where $\delta_{ij}$ is a unit matrix and k is the number of contours of each kind (e.g. OAR, PTV, ATR).

In an alternative embodiment, matrix $\alpha_{ij}$ and array $\beta_i$ are calculated by the following expressions:

$$\alpha_{ij} = p_{PTV} \alpha_{PTV} + p_{PTV}^c \alpha_{PTV}^c + p_{OAR}^c \alpha_{OAR}^c + p_{ATR}^c \alpha_{ATR}^c + p_{MLC}^{ave} \alpha_{MLC}^{ave} + p_{MLC}^{local} \alpha_{MLC}^{local}$$

$$\beta_{ij} = p_{PTV} \beta_{PTV} + p_{PTV}^c \beta_{PTV}^c + p_{OAR}^c \beta_{OAR}^c + p_{ATR}^c \beta_{ATR}^c + p_{MLC}^{ave} \beta_{MLC}^{ave}$$

where each individual term is defined according to the previously noted expressions.

The calculation of matrix $\alpha_{ij}$ and array $\beta_i$ is a fast calculation for which the arrays saved in fast memory in step 505 are used.

At step 610, the matrix α is inverted using a known fast matrix inversion algorithm, such as the lower-upper-diagonal (LUD) algorithm. Any suitably computationally efficient matrix inversion algorithm may be used at step 610.

At step 615, subprocess 600 checks matrix $\alpha_{ij}$ for near-linear dependence. This check is performed to ensure that there are no redundant or nearly redundant beamlets. If near-linear dependence is found, this is corrected at step 620 using a singular value decomposition (SVD) algorithm to appropriately condition matrix $\alpha_{ij}$.

In the absence of near-linear dependence, the beamlet weights are calculated, at step 625, as the product of inverted matrix $\alpha_{ij}$ with dose deposit array $\beta_i$. As part of step 625, the optimized beamlet weights are determined according to the solution of a linear system of equations (resulting from the product of inverted matrix $\alpha_{ij}^{-1}$ with dose deposit array $\beta_i$). This solution can be obtained by solving a system of N linear equations in N variables, where N is the number of beamlets.

At step 630, beamlet optimization subprocess 600 checks whether any of the beamlet weights have been calculated at step 625 to be negative. If there are any negative weights (i.e. negative beamlet intensities), the user is notified and, at step 635, is advised to adjust one or more of the importance coefficients in the objective function. Following adjustment of the importance coefficients, steps 605 to 625 are repeated until no negative beamlet weights are output from the calculations of step 625.

In embodiments that use the later described objective function, step 630 may be optional, since the new objective function terms greatly reduce the appearance of negative beamlet weights, making it very unlikely that any of the beamlet weights will be negative. However, this step may be implemented nonetheless in order to ensure that no negative beamlet weights appear, as may be the case when an unrealistic dose constraint is chosen for the OAR or the ATR, as explained above.

If the calculated beamlet weights are positive or zero, the optimized dose to be deposited in all organs and contours is recalculated with the optimized beamlet weights at step 640. At step 645, dose deposit statistics are calculated for all organs, contours and beamlets, including dose volume histogram (DVH) plots, for the optimized dose delivery plan.

Graphics, such as colour-coded dose distribution maps, are generated at step 650 according to the calculated dose statistics, where the colour-coded dose distribution is overlaid on the contours to provide an easy indication of the dose distribution across all contoured volumes. Example dose distribution maps and dose-volume histograms are shown in FIGS. 9A to 9D. Each colour-coded dose distribution graph is accompanied by a corresponding dose volume histogram to provide the user with a more accurate indication of whether the dose-volume constraints will be met by the proposed optimization of beamlet weights.

At step 655, the user is given the opportunity to indicate whether the planned dose distribution is satisfactory and, if not, is prompted to change the importance parameters at step 660. If the user elects to change the importance coefficients at step 660, steps 605 to 655 are re-executed until a satisfactory dose distribution is achieved.

Alternatively, if the user wishes to change some of the physical setup characteristics, such as the gantry angles, dose-volume constraints (or predetermined average dose constraint values), optimization process 100 returns (not shown) the user to subprocess 200 or 300, as appropriate.

Figure 7:
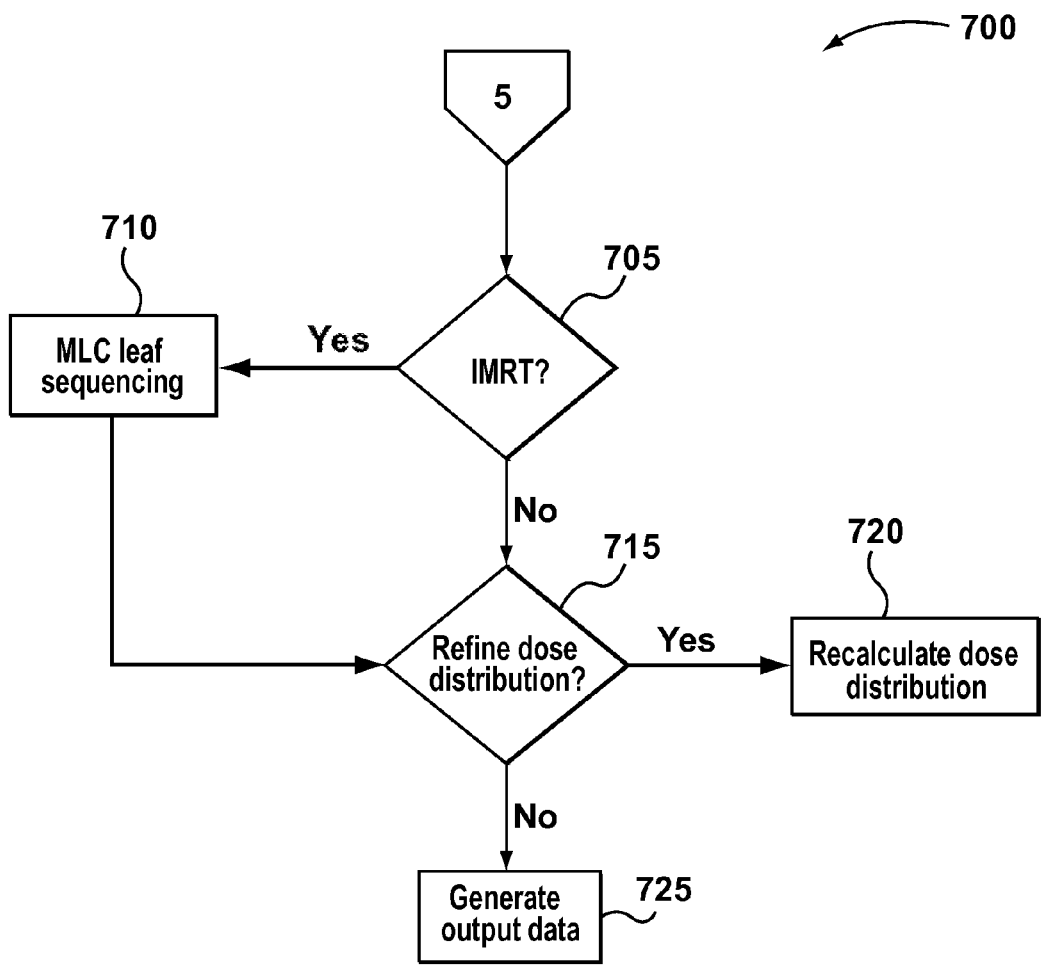
FIG. 7 is a flowchart of a results and statistics output sub-process of the process shown in FIG. 1.

Once the dose distribution is considered to be satisfactory, beamlet optimization subprocess 600 feeds into step 705 of result and statistics generation subprocess 700. FIGS. 6 and 7 are joined by reference indicator 5 in this respect.

Referring now to FIG. 7, results and statistics generation subprocess 700 is described. Results and statistics generation subprocess 700 generates an output of the optimized beamlet weights after the planned dose distribution is approved or refined.

At step 705, it is determined whether the desired form of radiation therapy is IMRT, and if so, generates leaf sequencing data for a multi-leaf collimator (MLC), at step 710. If the desired form of radiation therapy is Tomotherapy, a beam profile of collimated beamlets is generated (not shown) for each beam at each gantry angle and for each tumor slice.

At step 715, the user is again given the opportunity to refine the dose distribution, for example in order to suit the MLC leaf sequencing (if IMRT is used) or to accommodate other physical constraints imposed by the radiation therapy delivery system. Alternatively, refining dose distribution in order to suit the MLC leaf sequencing can be achieved by adjusting the importance parameter for the smoothing term(s). If the dose distribution requires refining, a more accurate dose deposition may be substituted for that previously defined and the dose distribution is recalculated at step 720.

If no further refinement of the dose distribution is required, an output data file is created at step 725, including optimized beamlet intensities 130 and leaf positions and sequences generated at step 710. Any beam, organ or contour statistics, together with data for displaying colour-coded dose distributions and dose-volume histograms may also be output (e.g. to a display) at step 725, if desired. The statistics and data for generating dose distribution graphs and histograms are stored in a memory of the computer system running optimization module 100 for user review and display and the optimized beamlet weights and MLC leaf positions and sequences are output to the radiation delivery system to begin radiation therapy treatment of the patient.

Figure 8:
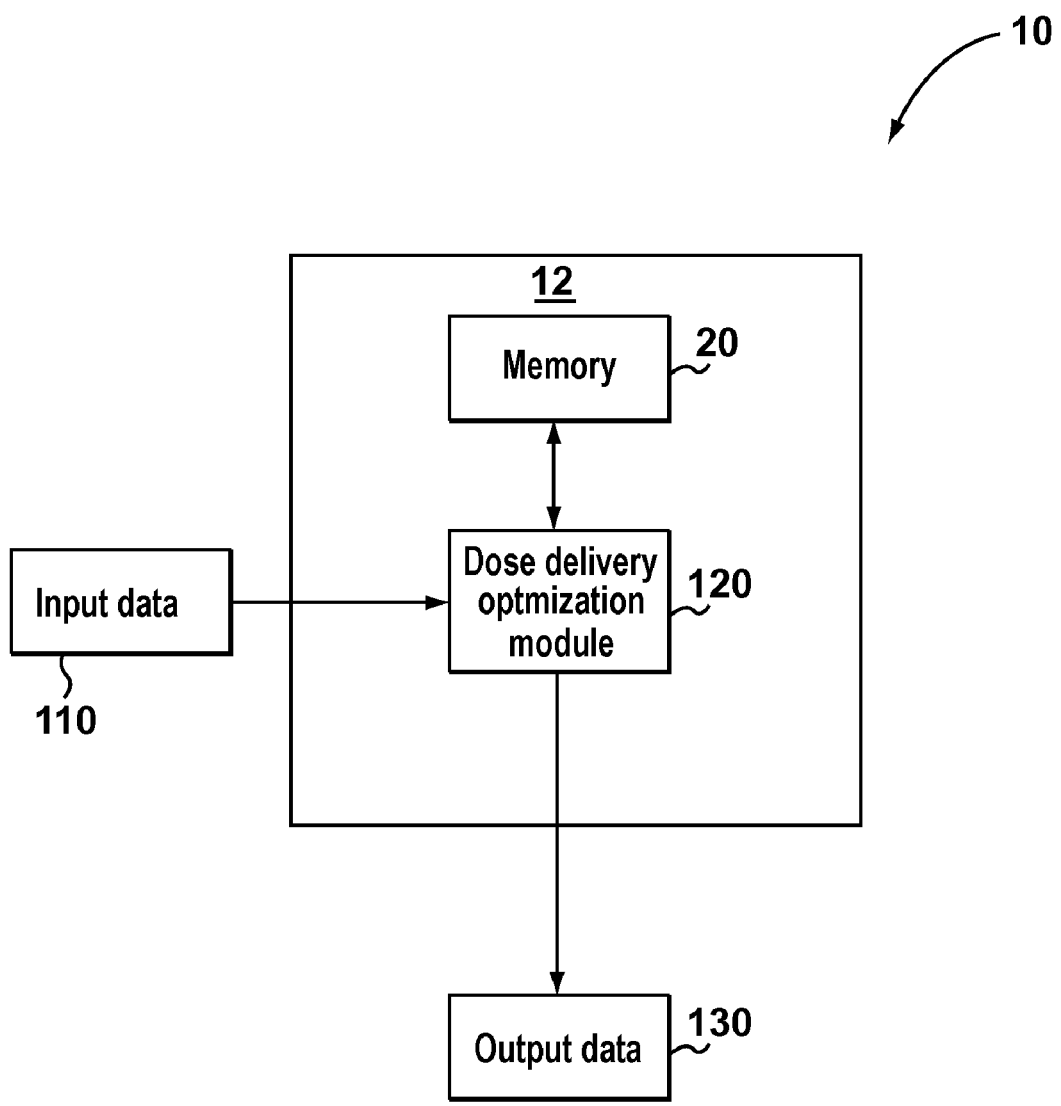
FIG. 8 is a block diagram of a system for dose delivery optimization according to described embodiments.

While the methods and subprocesses for optimization have been described above in relation to various embodiments, the invention may be embodied also in an optimization system 10, running optimization module 120 and configured to perform the described methods and subprocesses, as is shown in FIG. 8.

In FIG. 8, optimization system 10 includes a computer system 12 having memory 20 and optimization module 120 running as executable computer program instructions thereon. The computer program instructions are executed by one or more processors (not shown) within computer system 12. Memory 20 comprises fast memory, such as fast-access RAM, for storing arrays and matrices and calculation terms used during the optimization process 100. Memory 20 is also used to store statistics and/or calculations for generating dose-volume histograms and colour-coded dose distribution graphics. Memory 20 may also store dose-volume constraints, which may be incorporated into the terms of the objective function, such as for example $c^{OAR}(\%)$ and $c^{ATR}(\%)$. Memory 20 may include, or communicate with, secondary (slower) memory (not shown) to facilitate appropriate data storage or retrieval during process 100. Optimization module 120 uses memory 20 as required for its storage requirements.

Computer system 12 further includes normal computer peripherals (not shown), including graphics displays, keyboard, secondary memory and serial and network interfaces, as would normally be used for a computer system which receives input data 110 and generates corresponding output data 130.

In a further aspect, the invention may be embodied in computer program instructions (i.e. software for executing the described methods) stored on computer-readable storage media, such as a hard disk, CD-ROM or RAM.

While embodiments of the invention have been described in relation to dose delivery of radiation for radiation therapy treatment, it is to be understood that the optimization process 100 and optimization system 10 may be equally useful for planning optimized radiation delivery to body volumes other than those of human patients under treatment for cancerous tumors. For example, the described systems and methods may be employed for animals other than humans and may be employed for irradiating non-living tissue or material or organic matter where selective dose delivery of radiation is desired.

Figure 9A:
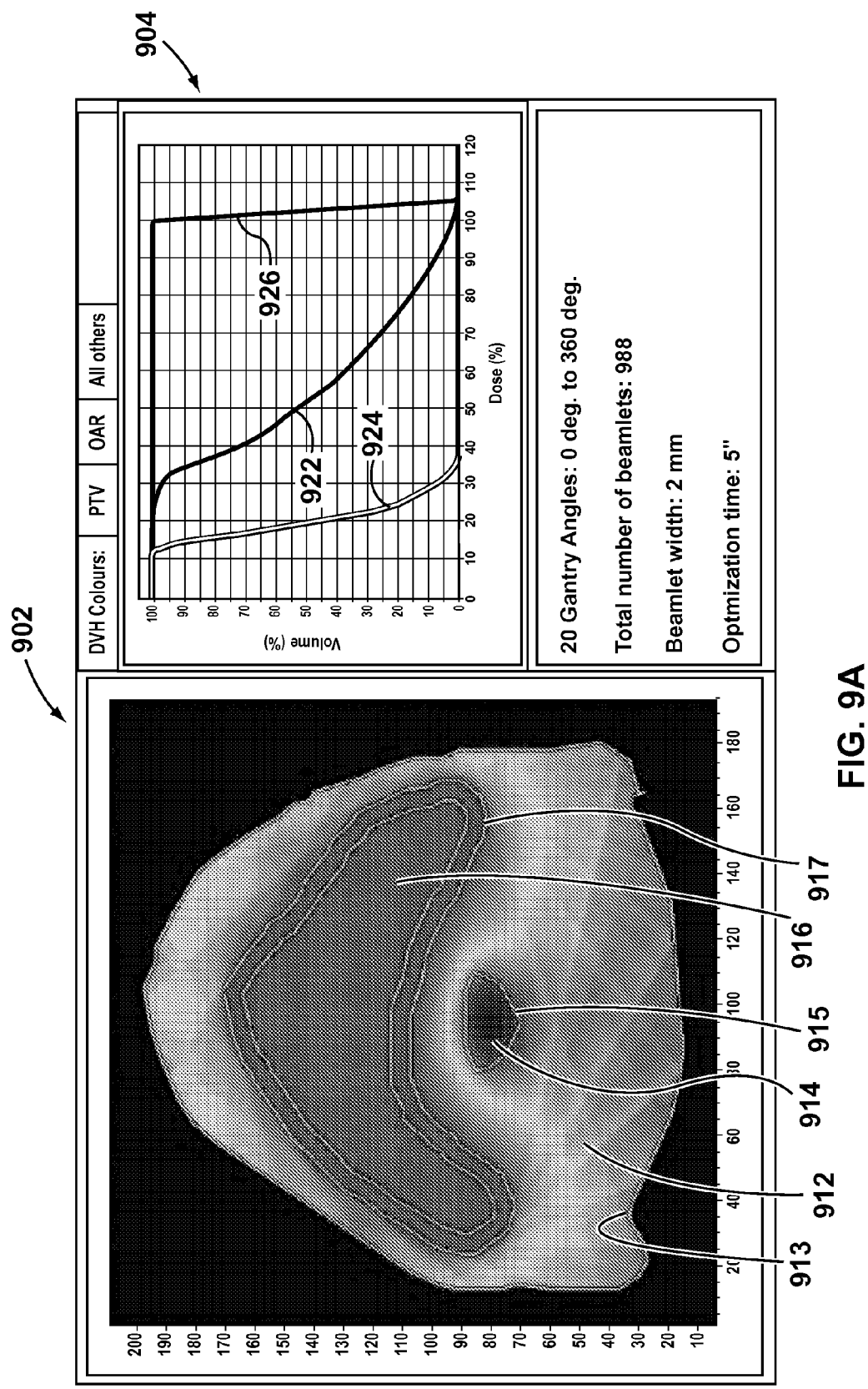
FIGS. 9A to 9D show example optimized dose distribution maps and corresponding dose-volume histograms.
Figure 9B:
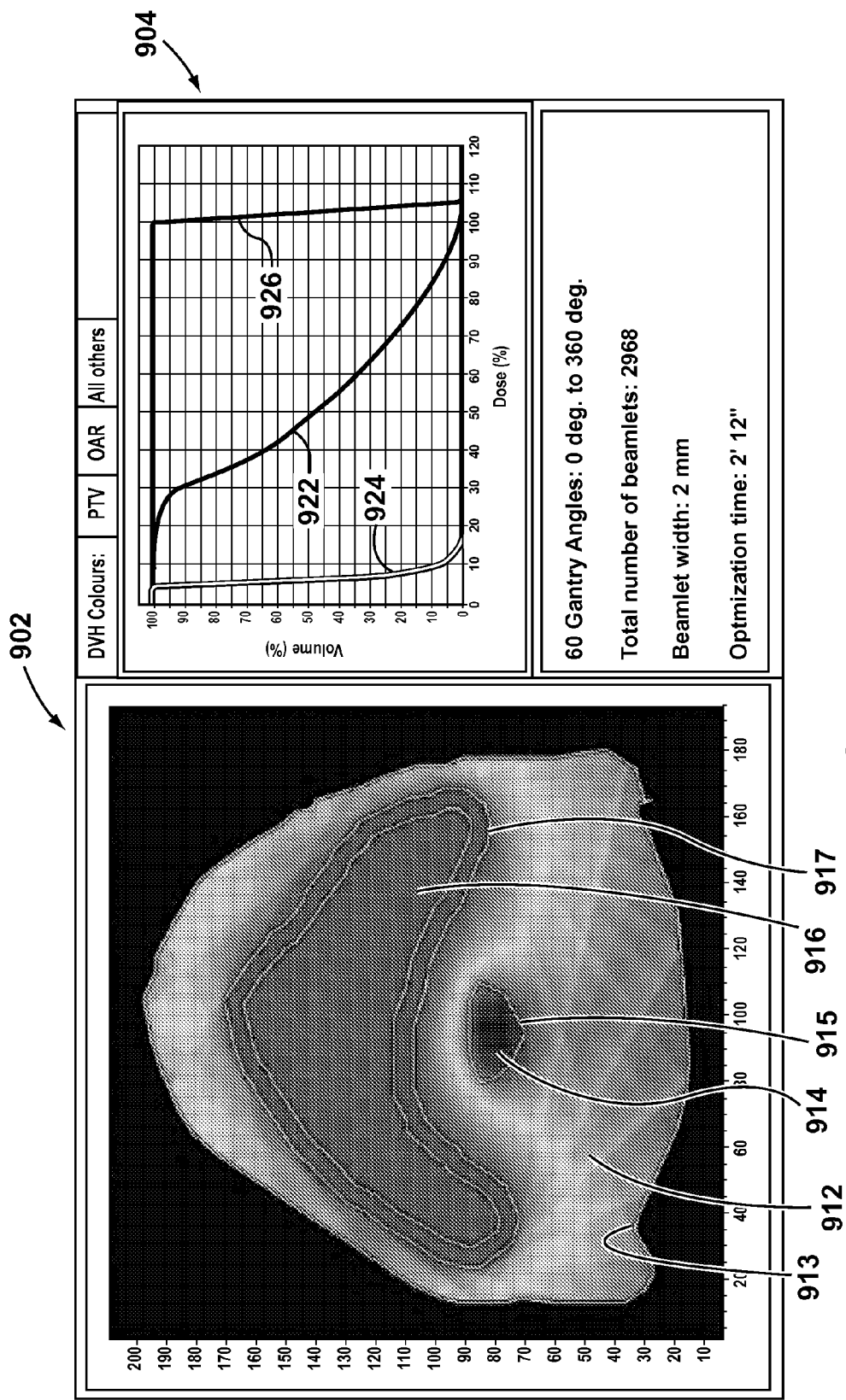

FIGS. 9A to 9D show example optimized dose distribution maps 902 and dose-volume histograms 904 for IMRT. FIGS. 9A and 9B show a dose distribution map 902 of a CT scan slice of a neck tumor. Dose distribution map 902 shows an outer body contour 913 enclosing all volumes of interest. OAR contour 915 encloses an OAR volume 914, which in this example is the spine. PTV contour 917 encloses a PTV volume 916, which is the neck tumor. The remaining volume within outer body contour 913, which is not within OAR and PTV volumes 914 and 916, is called the ATR volume 912.

As the example in FIG. 9A illustrates, it can be difficult to direct beams so as to deliver radiation to the PTV volume 916 without also directing some radiation towards the OAR volume 914. In this example, it is particularly important to minimize delivery of radiation to the spine as it is sensitive to radiation delivery and an excessive dose may result in damage to the spinal cord or nerve endings therein. Typically, dose-volume constraints for an OAR such as the spinal cord are such that none of the OAR volume should receive a dose in excess of about 45 Gy. If only a low number of gantry angles are employed in the optimization planning, this dose-volume constraint may not be able to be met, whereas if a larger number of gantry angles are employed, such a dose-volume constraint can be met. The greater computational efficiency achievable by the described embodiments of the invention enables a larger number of gantry angles to be employed, which results in a better conformal mapping of the dose delivery plan.

FIGS. 9A and 9B show the same ATR, OAR and PTV volumes and contours but, whereas FIG. 9A shows the output plan of an optimization using twenty gantry angles, FIG. 9B shows a plan using sixty gantry angles. In FIG. 9B, the OAR curve 924 of dose-volume histogram 904 shows that none of the OAR volume 914 receives more than 20% of the dose, as compared to the 40% indicated in FIG. 9A. The increase in the number of gantry angles allows for greater flexibility in optimizing the dose delivery plan so as to avoid irradiating the OAR while maximizing the radiation dose to the PTV. This increase in the number of gantry angles is enabled by the increased computational efficiency of the present optimization method.

In dose-volume histogram 904, ATR curve 922 indicates the dose-volume distribution of ATR volume 912, while PTV curve 926 indicates the dose-volume distribution to PTV volume 916.

Alternatively, as explained above, a dose-volume histogram may be interpreted as illustrating dose-volume constraints. Specifically, the dose-volume histogram curve may be interpreted as being a dose-volume histogram constraint curve, which provides that a percentage of a non-target volume should not receive more than a predetermined percentage of the dose prescribed to the PTV. For example, in the dose-volume histogram 902 shown in FIG. 9A, the OAR curve 924 may be interpreted as dose-volume constraint curve of OAR volume 914. The OAR curve 924 provides that that none of the OAR volume 914 receives more than 40% of the dose. This dose-volume constraint may be incorporated into an objective function term, such as for example by setting $c^{OAR}$(%) equal to 40%.

While the optimization is faster for fewer gantry angles (and thus fewer beamlets), for example in the order of 5 seconds, it is less optimized than the plan using sixty gantry angles in the sense that it delivers a higher average dose to the OAR volume 914. Conversely, while the optimization using sixty gantry angles is more accurate in avoiding the OAR volume 914, the time required for the optimization is greater, for example in the order of 2 minutes and 12 seconds.

Figure 9C:
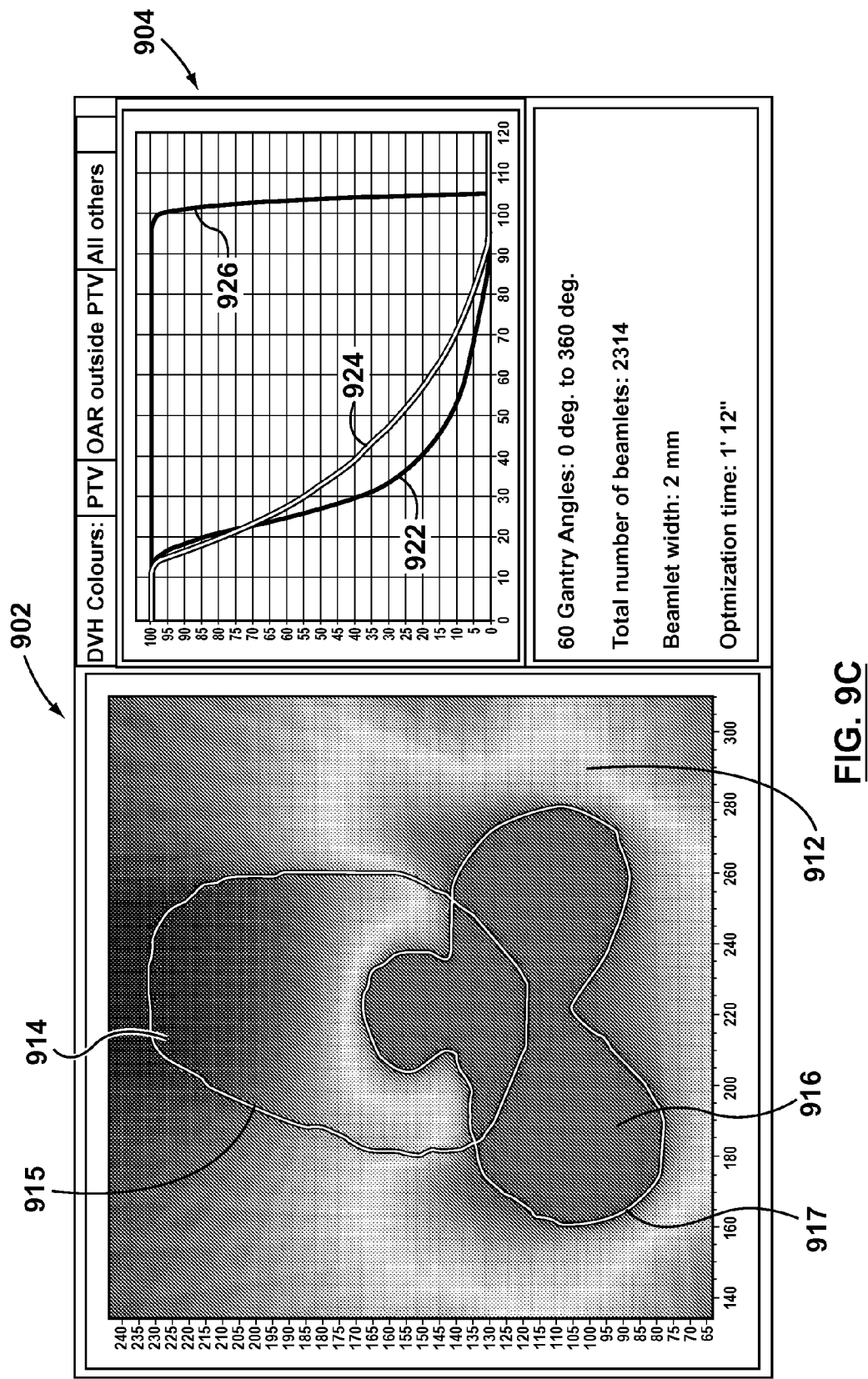
Figure 9D:
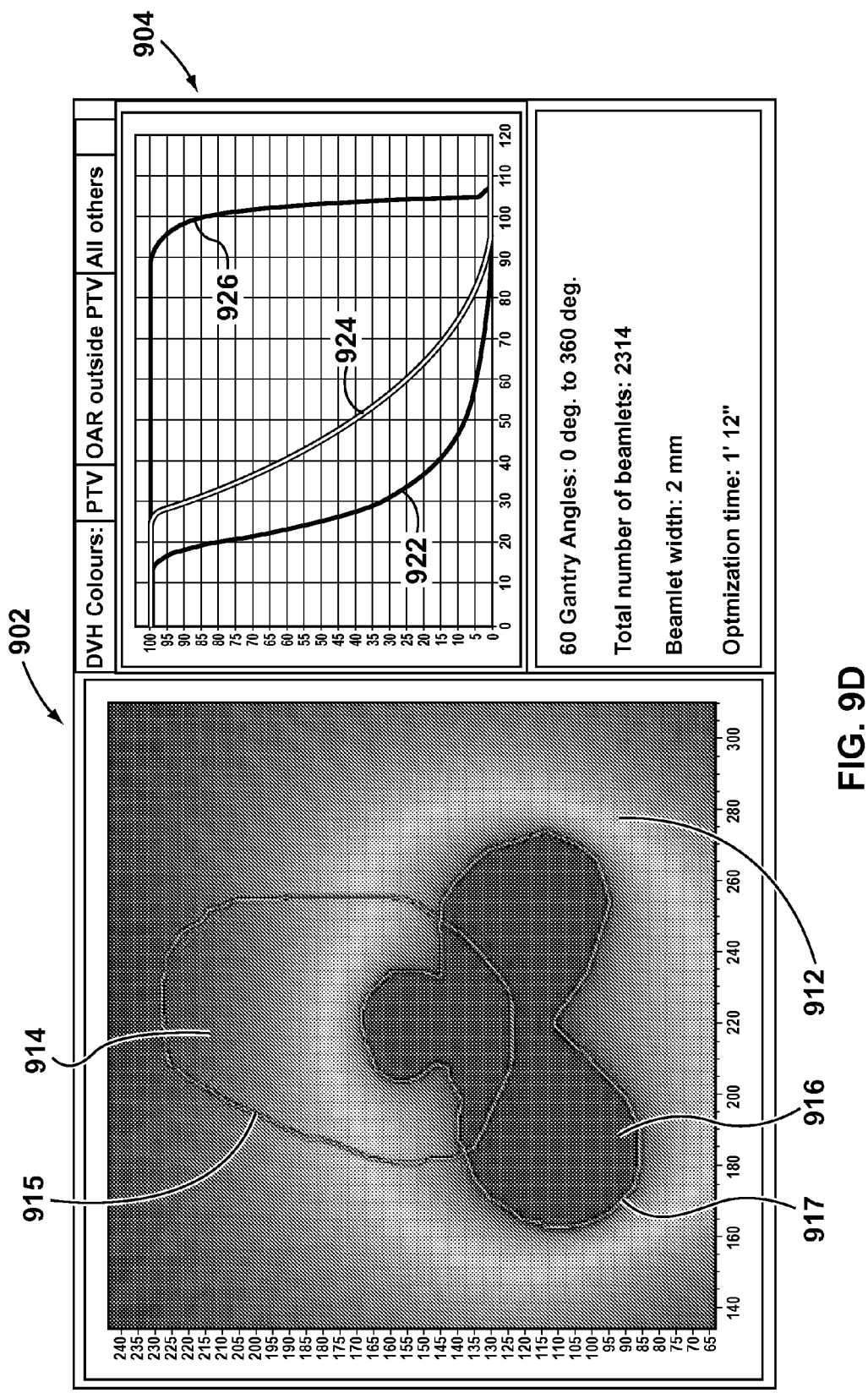

The reference indicators mentioned above in relation to FIGS. 9A and 9B are also applicable to FIGS. 9C and 9D.

FIGS. 9C and 9D show further examples of dose distribution maps 902 and corresponding dose-volume histograms 904. Outer body contour 913 is not shown in FIGS. 9C and 9D because in this example dose distribution map 902 is a close-up within a larger body volume. FIGS. 9C and 9D relate to a planned dose delivery to a prostate tumor, indicated by PTV volume 916. In this example, the OAR volume 914 is the bladder. As can be seen from FIGS. 9C and 9D, the OAR body contour 915 overlaps the PTV contour 917 and therefore it is not possible to minimize dose delivery to the OAR to the same degree as would be possible where the contours and volumes did not overlap.

The optimizations shown in FIGS. 9C and 9D use the same number of IMRT gantry angles and beamlets, with the same beamlet width of 2 mm. The primary difference between FIGS. 9C and 9D is that the optimization shown in FIG. 9D was designed to provide a highly conformal dose distribution to the PTV, with less importance being given to irradiating the OAR. A comparison of OAR curves 924 in FIGS. 9C and 9D indicates that the OAR volume 914 in FIG. 9D received a higher average dose than that of FIG. 9C, primarily because of the lower importance attributed to minimizing irradiation of the OAR in the optimization shown in FIG. 9D. Thus, manipulation of importance coefficients can have a significant effect on the resultant dose distribution within the PTV and OAR.

In this description, certain terms have been used interchangeably. For example, beamlet weights and beamlet intensities have been used interchangeably and are intended to have the same meaning. Similarly, importance parameters and importance coefficients have been used interchangeably and are intended to have the same meaning. Also, some terms used in this description may be called by other names in related technical papers, although the meaning is the same. For example, the term objective function used herein may be called a cost function by others. Similarly, the term fluence is used elsewhere for describing beamlet weights or intensities. It is intended that this description should cover all terms having the same meaning, as would be understood by the skilled person, as the terms used herein.

The invention claimed is:

1. A method of optimizing planned dose delivery of radiation comprising the steps of:

determining an objective function to be used for mapping radiation beams to a body volume comprising at least one target volume, and at least one non-target volume, the objective function comprising a first term related to the at least one target volume and a second term related to the at least one non-target volume;

determining an optimal set of weights of beamlets using the objective function whereby beams, comprising a plurality of beamlets, mapped to pass through the at least one non-target volume, comprising a plurality of non-target volume portions, are limited such that the second term is zero only when a product of the weight of a beamlet mapped to pass through a non-target volume portion and the dose deposited by said beamlet is equal to a first predetermined average dose constraint value for the respective non-target volume portion, for all beamlets mapped to pass through the at least one non-target volume; and delivering radiation based on the determined optimal set of weights of beamlets.

2. The method of claim 1, wherein the first term comprises, for all of a plurality of target volume portions of the target volume, a target volume sum of beamlet sums related to respective target volume portions, each beamlet sum being a sum of a square of the difference between the product of the weight of the beamlet with a planned radiation dose deposited by the beamlet at the respective target volume portion and an average dose per beamlet at the respective target volume portion.

3. The method of claim 1, wherein the second term comprises, for all of the plurality of non-target volume portions, a non-target volume sum of beamlet sums related to respective non-target volume portions, each beamlet sum being a sum of a square of the difference between the product of the weight of the beamlet with a planned radiation dose to be deposited by the beamlet at the respective non-target volume portion and the first predetermined average dose constraint value for the respective non-target volume portion.

4. The method of claim 1, wherein the first predetermined average dose constraint value for the respective non-target volume portion is equal to the product of a prescribed radiation dose deposit for the target volume with a percentage of the prescribed radiation dose deposit for the target volume permitted in the non-target volume divided by the number of beamlets mapped to pass through the respective non-target volume portion.

5. The method of claim 1, wherein the objective function further comprises a third term related to at least one organ-at-risk (OAR) volume, whereby beams, comprising a plurality of beamlets, mapped to pass through the at least one OAR volume, comprising a plurality of OAR volume portions, are limited such that the third term is zero only when a product of the weight of a beam let mapped to pass through an OAR volume portion and the dose deposited by said beamlet is equal to a second predetermined average dose constraint value for the respective OAR volume portion, for all beamlets mapped to pass through the OAR volume.

6. The method of claim 5, wherein the third term comprises, for all of the plurality of OAR volume portions, an OAR volume sum of beamlet sums related to respective OAR volume portions, each beamlet sum being a sum of a square of the difference between the product of the weight of the beamlet with the planned radiation dose deposit to be deposited by the beamlet at the respective OAR volume portion and the second predetermined average dose constraint value for the respective OAR volume portion.

7. The method of claim 5, wherein the second predetermined average dose constraint value for the respective OAR volume portion is equal to the product of a prescribed radiation dose deposit for the target volume with a percentage of the prescribed dose deposit for the target volume permitted in the OAR volume over the number of beamlets mapped to pass through the respective OAR volume portion.

8. The method of claim 5, wherein the second predetermined average dose constraint value for the respective OAR volume portion is determined according to constraints derived from a dose-volume constraint curve.

9. The method of claim 1, wherein the objective function further comprises a smoothing term for biasing the weight of the beamlets of a beam mapped to pass through the at least one target volume and the at least one non-target volume towards a uniform distribution within the respective beam.

10. The method of claim 9, wherein the smoothing term is an average smoothing term of the form:

$$O_{MLC}^{ave} = \frac{1}{2} \sum_{k}^{allbeams} \sum_{i}^{inbeamk} (w_i - \langle w \rangle_k)^2$$

where $O_{MLC}^{ave}$ is the average smoothing term, and $w_i$ is the weight of beamlet i in beam k, and $\langle w \rangle_k$ is the average weight of all beamlets in beam k.

11. The method of claim 9, wherein the smoothing term is a local smoothing term of the form:

$$O_{MLC}^{local} = \sum_{k}^{allbeams} \frac{1}{N_k} \sum_{i,j}^{inbeamk} (w_j - w_j)^2$$

where $O_{MLC}^{local}$ is the local smoothing term, and $w_i$ is the weight of beamlet i, and $w_j$ is the weight of beamlet j, and i and j are adjacent beamlets in beam k.

12. The method of claim 1, wherein the step of determining an optimal set of beamlet weights includes solving a linear system of equations to determine the intensities of the beamlets.

13. The method of claim 12, wherein the linear system of equations is derived from a first derivative of the objective function.

14. The method of claim 12, wherein the solution of the linear system of equations is generated using matrix inversion of a beamlet intersection matrix for each beamlet.

15. The method of claim 14, wherein the solution of the linear system of equations is generated by the product of the inverted beamlet intersection matrix with a beamlet dose deposit array.

16. The method of claim 14, wherein the beamlet intersection matrix comprises at least one term corresponding to the target volume and at least one term corresponding to the non-target volume, each being scaled by a respective importance parameter.

17. The method of claim 16, wherein the beamlet intersection matrix further comprises a smoothing term having a smoothing importance parameter for scaling the smoothing term.

18. The method of claim 17, wherein the smoothing importance parameter is determined according to a user-configurable value.

19. The method of claim 16, wherein each importance parameter for scaling the at least one term corresponding to the target volume and the at least one term corresponding to the non-target volume respectively, is determined according to a function of position within the respective target and non-target volume.

20. The method of claim 16, wherein each importance parameter for scaling the at least one term corresponding to the target volume and the at least one term corresponding to the non-target volume respectively, has a predetermined value.

21. The method of claim 1, further comprising:
receiving contour data relating to a two-dimensional contour of the at least one target volume or the at least one non-target volume;
determining from the contour data whether the contour is oriented clockwise or anti-clockwise; and
when the contour is determined to be anti-clockwise, changing the order of the contour data so that the contour is oriented clockwise.

22. The method of claim 21, wherein determining whether the contour is oriented clockwise or anti-clockwise further comprises:
determining a topmost vertex of the contour;
determining a lowermost vertex of the contour;
determining a rightmost vertex of the contour that is neither the topmost or lowermost vertex;
determining a leftmost vertex of the contour that is neither the topmost or lowermost vertex; and
determining the contour orientation according to the relative clockwise order of the topmost, lowermost, rightmost and leftmost vertices with respect to each other.

23. The method of claim 21, further comprising:
extrapolating a continuous contour from the contour data;
determining all right and left boundaries of the continuous contour; and
determining a cell of the body volume to be within the continuous contour when the cell lies between a facing pair of right and left boundaries.

24. The method of claim 23, wherein a boundary is determined to be a left boundary when the contour data indicates an upwardly extending sequence of contour points and a boundary is determined to be a right boundary when the contour data indicates a downwardly extending sequence of contour points.

25. The method of claim 1, wherein said body volume is virtually divided into a plurality of cells of a predetermined size and said radiation beams are mapped to said body volume such that fractions of the radiation beams are dimensioned proportionally to the size of said cells.

26. The method of claim 25, wherein said fractions are resolved into linearly sequential portions of non-uniform size.

27. The method of claim 26, wherein a linear dimension of said sequential portions is uniform and is 1 to 2 times a width dimension of said cells.

28. The method of claim 27, wherein said linear dimension is about 1.25 times said width dimension.

29. The method of claim 1, wherein the dose delivery of radiation comprises intensity-modulated radiation therapy.

30. The method of claim 1, wherein the dose delivery of radiation comprises Tomotherapy.

31. The method of claim 1 wherein the first predetermined average dose constraint value for the respective non-target volume portion is determined according to constraints derived from a dose-volume constraint curve.

32. The method of claim 1, wherein each weight of the determined optimal set of weights of beamlets is greater or equal to zero.

33. The method of claim 1, wherein determining the optimal set of weights of beamlets comprises determining a minimum of the objective function.

34. The method of claim 1, wherein determining the optimal set of weights of beamlets comprises determining a maximum of the objective function.

35. A method of providing optimized radiation dose delivery, comprising the step of:
determining an objective function to be used for mapping radiation beams, comprising a plurality of beamlets, to at least one target volume, the objective function having a smoothing term for biasing the weight of beamlets, for a respective beam mapped to pass through the at least one target volume, towards a uniform distribution within the respective beam; and
providing radiation based on the objective function;
wherein the smoothing term is selected from the smoothing terms consisting of:
an average smoothing term of the form:

$$O_{MLC}^{ave} = \frac{1}{2} \sum_{k}^{allbeams} \sum_{i}^{allbeamlets \atop inbeamk} (w_i - \langle w \rangle_k)^2$$

where $O_{MLC}^{ave}$ is the smoothing term, and $w_i$ is the weight of beamlet i in beam k, and $\langle w \rangle_k$ is the average weight of all beamlets in beam k; and
a local smoothing term of the form:

$$O_{MLC}^{local} = \sum_{k}^{allbeams} \frac{1}{N_k} \sum_{i,j}^{allbeamlets \atop inbeamk} (w_i - w_j)^2$$

where $O_{MLC}^{local}$ is the smoothing term, and $w_i$ is the weight of beamlet i, and $w_j$ is the weight of beamlet j, and i and j are adjacent beamlets in beam k.

36. The method of claim 35, wherein providing radiation comprises providing intensity-modulated radiation therapy.

37. The method of claim 35, wherein providing radiation comprises providing Tomotherapy.

38. A sistem for optimizing dose delivery of radiation Comprising:
an optimization module for determining an objective function to be used for mapping radiation beams to a body volume comprising at least one target volume, and at least one non-target volume, the objective function comprising a first term related to the at least one target volume and a second term related to the at least one non-target volume, the optimization module being arranged to determine an optimal set of weights of beamlets using the objective function whereby beams, comprising a plurality of beamlets, mapped to pass through the at least one non-target volume, comprising a plurality of non-target volume portions, are limited such that the second term is zero only when a product of the weight of a beamlet mapped to pass through a non-target volume portion and the dose deposited by said beamlet is equal to a predetermined average dose constraint value for the respective non-target volume portion, for all beamlets mapped to pass through the at least one non-target volume; and
an output operably associated with the optimization module for providing data to a radiation delivery apparatus for delivering radiation to the body volume based on the determined optimal set of weights of beamlets.

39. Computer readable storage having stored thereon computer program instructions executable on a computer system for causing the computer system to perform a method comprising:
determining an objective function to be used for mapping radiation beams for a body volume comprising at least one target volume and at least one non-target volume, the objective function comprising a first term related to the at least one target volume and a second term related to the at least one non-target volume;
determining an optimal set of weights of beamlets using the objective function whereby beams, comprising a plurality of beamlets, mapped to pass through the at least one non-target volume, comprising a plurality of non-target volume portions, are limited such that the second term is zero only when a product of the weight of a beamlet mapped to pass through a non-target volume portion and the dose deposited by said beamlet is equal to a first predetermined average dose constraint value for the respective non-target volume portion, for all beamlets mapped to pass through the at least one non-target volume; and
delivering radiation based on the determined optimal set of weights of beamlets.

* * * * *